(12) United States Patent
Coley et al.

(10) Patent No.: US 10,622,098 B2
(45) Date of Patent: Apr. 14, 2020

(54) SYSTEMS AND METHODS FOR PREDICTING CHEMICAL REACTIONS

(71) Applicant: Massachusetts Institute of Technology, Cambridge, MA (US)

(72) Inventors: Connor Wilson Coley, Cambridge, MA (US); Klavs F. Jensen, Lexington, MA (US); Regina Barzilay, Cambridge, MA (US); Tommi S. Jaakkola, Burlington, MA (US); Wengong Jin, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 2 days.

(21) Appl. No.: 16/116,805

(22) Filed: Aug. 29, 2018

(65) Prior Publication Data

US 2020/0027528 A1 Jan. 23, 2020

Related U.S. Application Data

(60) Provisional application No. 62/557,519, filed on Sep. 12, 2017.

(51) Int. Cl.
*G01N 21/75* (2006.01)
*G01N 31/22* (2006.01)
(Continued)

(52) U.S. Cl.
CPC .............. *G16C 20/10* (2019.02); *G16C 20/20* (2019.02); *G16C 20/50* (2019.02)

(58) Field of Classification Search
CPC ........ G16C 20/10; G16C 20/20; G16C 20/50; G01N 21/75
(Continued)

(56) References Cited

U.S. PATENT DOCUMENTS

2002/0111782 A1* 8/2002 Klaffke .................. G05B 17/02
703/12
2004/0220749 A1 11/2004 Miller et al.
(Continued)

OTHER PUBLICATIONS

[No Author Listed], SMARTS—A Language for Describing Molecular Patterns. Daylight Chemical Information Systems. 2008; 7 pages. Retrieved from the Internet: http://www.daylight.com/dayhtml/doc/theory/theory.smarts.html Last accessed Apr. 12, 2019.
(Continued)

*Primary Examiner* — John H Le
(74) *Attorney, Agent, or Firm* — Wolf, Greenfield & Sacks, P.C.

(57) ABSTRACT

Techniques for predicting a chemical reaction that includes a set of input molecules. The techniques may include obtaining input molecule information identifying the set of input molecules and predicting at least one chemical reaction that include a transformation between the set of input molecules and a set of output molecules by modifying at least one reaction center of the set of input molecules. The predicting of the at least one chemical reaction may be performed at least in part by using the input molecule information and at least one statistical model relating properties of atoms outside a region of a molecule to reactivity of the molecule at the region to identify the at least one reaction center. The techniques further include outputting information indicating the set of output molecules.

32 Claims, 11 Drawing Sheets

(51) Int. Cl.
  *G16C 20/10* (2019.01)
  *G16C 20/20* (2019.01)
  *G16C 20/50* (2019.01)
(58) Field of Classification Search
  USPC .................. 702/22, 30; 324/309; 703/12
  See application file for complete search history.

(56) References Cited

U.S. PATENT DOCUMENTS

2016/0131603 A1   5/2016   Van der Mei et al.
2017/0121852 A1   5/2017   Siva Kimar et al.

OTHER PUBLICATIONS

Bahdanau et al., Neural machine translation by jointly learning to align and translate. Published as a conference paper at ICLR 2015. May 19, 2016; 15 pages. arXiv:1409.0473. 2014.
Balaban et al., Applications of graph theory in chemistry. J. Chem. Inf. Comput. Sci. 1985; 25:334-343.
Bøgevig et al., Route Design in the 21$^{st}$ Century: The ICSYNTH Software Tool as an Idea Generator for Synthesis Prediction. Organic Process Research & Development. 2015;19: 357-368.
Chen et al., No electron left behind: a rule-based expert system to predict chemical reactions and reaction mechanisms. Journal of chemical information and modeling. 2009; 49(9):2034-2043.
Christ et al., Mining electronic laboratory notebooks: analysis, retrosynthesis, and reaction based enumeration. Journal of chemical information and modeling 2012; 52(7): 1745-1756.
Cook et al., Computer-aided synthesis design: 40 years on. Wiley Interdiscip. Rev. WIREs Comput. Mol. Sci. 2012; 2:79-107.
Corey et al., Computer-assisted synthetic analysis. Synthetic strategies based on appendages and the use of reconnective transforms. Journal of American Chemical Society. Jan. 7, 1976; 98(1):189-203.
Dai et al., Discriminative embeddings of latent variable models for structured data. Proceedings of the 33$^{rd}$ International Conference on Machine Learning. 2016; JMLR: W&CP vol. 48: 10 pages. arXiv preprint arXiv: 2016; 1603.05629.
Duvenaud et al., Convolutional networks on graphs for learning molecular fingerprints. Advances in neural information processing systems. 2015; pp. 2224-2232.
Fujita, Description of organic reactions based on imaginary transition structures. Introduction of new concepts. J. Chem. Inf. Comput Sci. 1986: 26:205-212.
Gasteiger et al. A new treatment of chemical reactivity: Development of EROS, an expert system for reaction prediction and synthesis design. Topics in Current Chemistry. Organic Synthesis, Reactions and Mechanisms. Springer, Berlin, Heidelberg. 1987; 19-73.
Hartenfeller et al., A collection of robust organic synthesis reactions for In Silico molecule design. Journal of Chemical Information and Modeling. 2011;51(12):3093-3098.
Kayala et al., ReactionPredictor: Prediction of Complex Chemical Reactions at the Mechanistic Level using Machine Learning. Journal of Chemical Information and Modeling. 2012; 52:2526-2540.
Kearnes et al., Molecular graph convolutions: moving beyond fingerprints. Journal of computer-aided molecular design. 2016; 30(8):595-608.
Kingma et al., Adam: A method for stochastic optimization. Published as a conference paper at International Conference on Learning Representation 2015. 2015; 15 pages.
Landrum, RDKit: Open-source cheminformatics software. Open-Source Cheminformatics and Machine Learning. Online Httpwww Rdkit Org Accessed (2006), (available at http://rdkit.org) Last accessed May 16, 2019. 2 pages.
Law et al., Route designer: a retrosynthetic analysis tool utilizing automated retrosynthetic rule generation. J. Chem. Inf. Model. 2009; 49(3):593-602.

Lei et al., Deriving neural architectures from sequence and graph kernels. Proceedings of 34$^{th}$ International Conference on Machine Learning (ICML). 2017; 22 pages.
Lei et al., Rationalizing Neural Predictions. Computer Science and Artificial Intelligence Laboratory. Massachusetts Institute of Technology. 2016; 11 pages. arXiv:1606.04155.
Liu et al., Retrosynthetic reaction prediction using neural sequence-to-sequence models. arXiv preprint arXiv: 1706.01643 2017; 20 pages.
Lowe, Extraction of chemical structures and reactions from the literature. Doctoral Thesis, Pembroke College, University of Cambridge, Department of Chemistry. 2012; 210 pages.
Nam et al., Linking the Neural Machine Translation and the Prediction of Organic Chemistry Reactions. arXiv preprint arXiv:1612.09529 2016; 19 pages.
Pensak et al., LHASA-Logic and Heuristics Applied to Synthetic Analysis. Computer-Assisted Organic Synthesis. ACS Symposium Series: American Chemical Society. 1977; 61: 1-32.
Ramakrishnan et al. Big Data Meets Quantum Chemistry Approximations: The Δ-Machine Learning Approach. J. Chem. Theory Comput. 2015; 11:2087-2096.
Salatin et al., Computer-Assisted Mechanistic Evaluation of Organic Reactions. 1. Overview. J. Org. Chem. May 23, 1980; 45(11):2043-2051.
Santanilla et al., Nanomole-scale High-throughput Chemistry for the Synthesis of Complex Molecules. Science. Jan. 2, 2015; 347(6217):49-53.
Satoh et al., SOPHIA, a Knowledge Base-guided Reaction Prediction System-utilization of a Knowledge Base Derived from a Reaction Database. J. Chem. Inf. Comput. Sci. 1995; 35:34-44.
Segler et al., Neural-symbolic machine learning for retrosynthesis and reaction prediction. Chemistry—A European Journal. 2017; 23:5966-5971.
Shervashidze et al., Weisfeiler-Lehman Graph Kernels. J. Mach. Learn. Res. 2011; 12: 2539-2561.
Socorro et al., ROBIA: a Reaction Prediction Program. Org Lett. 2005; 7(16):3541-3544.
Szymkuć et al., Computer-assisted synthetic planning: The end of the beginning. Angewandte Chemie Int. Ed. 2016;55(20):5904-5937.
Todd, Computer-aided organic synthesis. Chemical Society Reviews. 2005; 34(3):247-266.
Ugi et al., Computer-Assisted Solution of Chemical Problems—The Historical Development and the Present State of the Art of a New Discipline of Chemistry. Angew. Chem. Int. Ed. Engl. 1993; 32:201-227.
Warr, A short review of chemical reaction database systems, computer-aided synthesis design, reaction prediction and synthetic feasibility. Molecular Informatics. 2014; 33:469-476.
Wei et al., Neural networks for the prediction of organic chemistry reactions. ACS Central Science. 2016; 2(10):725-732.
Weininger, Smiles, a Chemical Language and Information System. 1. Introduction to Methodology and Encoding Rules. J. Chem. Inf. Comput. Sci. 1988; 28(1):31-36.
PCT/US2018/050642, Nov. 19, 2018, International Search Report and Written Opinion.
International Search Report and Written Opinion dated Nov. 19, 2018 in connection with International Application No. PCT/US2018/050642.
Coley et al., Prediction of Organic Reaction Outcomes Using Machine Learning. American Chemical Society: Central Science. Apr. 18, 2017; 3:434-443.
Karickhoff et al., Predicting Chemical Reactivity by Computer. Environmental Toxicology and Chemistry. 1991; 10:1405-1416.
Kayala et al., Learning to Predict Chemical Reactions. Journal of Chemical Information and Modeling. 2011; 51:2209-2222.
Liu et al., Retrosynthetic Reaction Prediction Using Neural Sequence-to-Sequence Models. American Chemical Society: Central Science. Sep. 5, 2017; 3:1103-1113.

* cited by examiner

SYSTEMS AND METHODS FOR PREDICTING CHEMICAL REACTIONS

RELATED APPLICATIONS

The present application claims the benefit under 35 U.S.C. § 119(e) to U.S. Application Ser. No. 62/557,519, filed Sep. 12, 2017 and titled "SYSTEMS AND METHODS FOR PREDICTING CHEMICAL REACTIONS," which is incorporated herein by reference in its entirety.

FEDERALLY SPONSORED RESEARCH

This invention was made with Government support under Grant No. W911NF-16-2-0023 awarded by the Army Research Office. The Government has certain rights in the invention.

FIELD

Aspects of the technology described herein relate to simulating chemical reactions by predicting possible reaction transformations on input molecules (e.g., reactants) into new molecules (e.g., products).

BACKGROUND

One of the challenges faced in chemistry, particularly in organic chemistry, is the ability to predict a chemical reaction from a set of reactants and product(s) that form as a result of the chemical reaction. Predicting the outcome of a chemical reaction may reduce time arising from repeated experimentation and improve design and development of new chemical processes and molecules. Experienced chemists may apply their knowledge of chemistry reactions to an unknown set of reactants and conditions to predict how a chemical reaction is likely to proceed. As the complexity of the chemical reaction grows, correctly predicting the end product(s) as an outcome of a chemical reaction for a set of reactants may become increasingly difficult. Computational techniques for predicting chemical reactions may be used to analyze a set of reactants to determine product(s) that form as a result of a chemical reaction using the set of reactants. However, for some chemical reactions, experimentally conducting the chemical reaction remains the primary method for analyzing the chemical reaction.

SUMMARY

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining input molecule information identifying at least one input molecule, predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center, and outputting information indicating the at least one output molecule.

Some embodiments are directed to at least one non-transitory computer-readable storage medium storing processor-executable instructions that, when executed by at least one hardware processor, cause the at least one hardware processor to perform: obtaining input molecule information identifying at least one input molecule, predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center, and outputting information indicating the at least one output molecule.

Some embodiments are directed to a method, comprising: obtaining input molecule information identifying at least one input molecule, predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center, and outputting information indicating the at least one output molecule.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining input molecule information identifying at least one input molecule, wherein the input molecule information identifies individual atoms of at least one input molecule and types of bonds between atoms in the at least one input molecule, identifying at least one reaction center in the at least one input molecule, the identifying performed at least in part by using the input molecule information and at least one statistical model relating properties of atoms proximate to an atom and properties of atoms distal to the atom to reactivity of the atom, and outputting information indicating the at least one reaction center.

Some embodiments are directed to at least one non-transitory computer-readable storage medium storing processor-executable instructions that, when executed by at least one hardware processor, cause the at least one hardware processor to perform: obtaining input molecule information identifying at least one input molecule, wherein the input molecule information identifies individual atoms of at least one input molecule and types of bonds between atoms in the at least one input molecule, identifying at least one reaction center in the at least one input molecule, the identifying performed at least in part by using the input molecule information and at least one statistical model relating properties of atoms proximate to an atom and properties of atoms distal to the atom to reactivity of the atom, and outputting information indicating the at least one reaction center.

Some embodiments are directed to a method, comprising: obtaining input molecule information identifying at least one input molecule, wherein the input molecule information identifies individual atoms of at least one input molecule and types of bonds between atoms in the at least one input molecule, identifying at least one reaction center in the at least one input molecule, the identifying performed at least in part by using the input molecule information and at least one statistical model relating properties of atoms proximate to an atom and properties of atoms distal to the atom to reactivity of the atom, and outputting information indicating the at least one reaction center.

BRIEF DESCRIPTION OF DRAWINGS

Various aspects and embodiments will be described with reference to the following figures. The figures are not necessarily drawn to scale.

DETAILED DESCRIPTION

Figure 1:
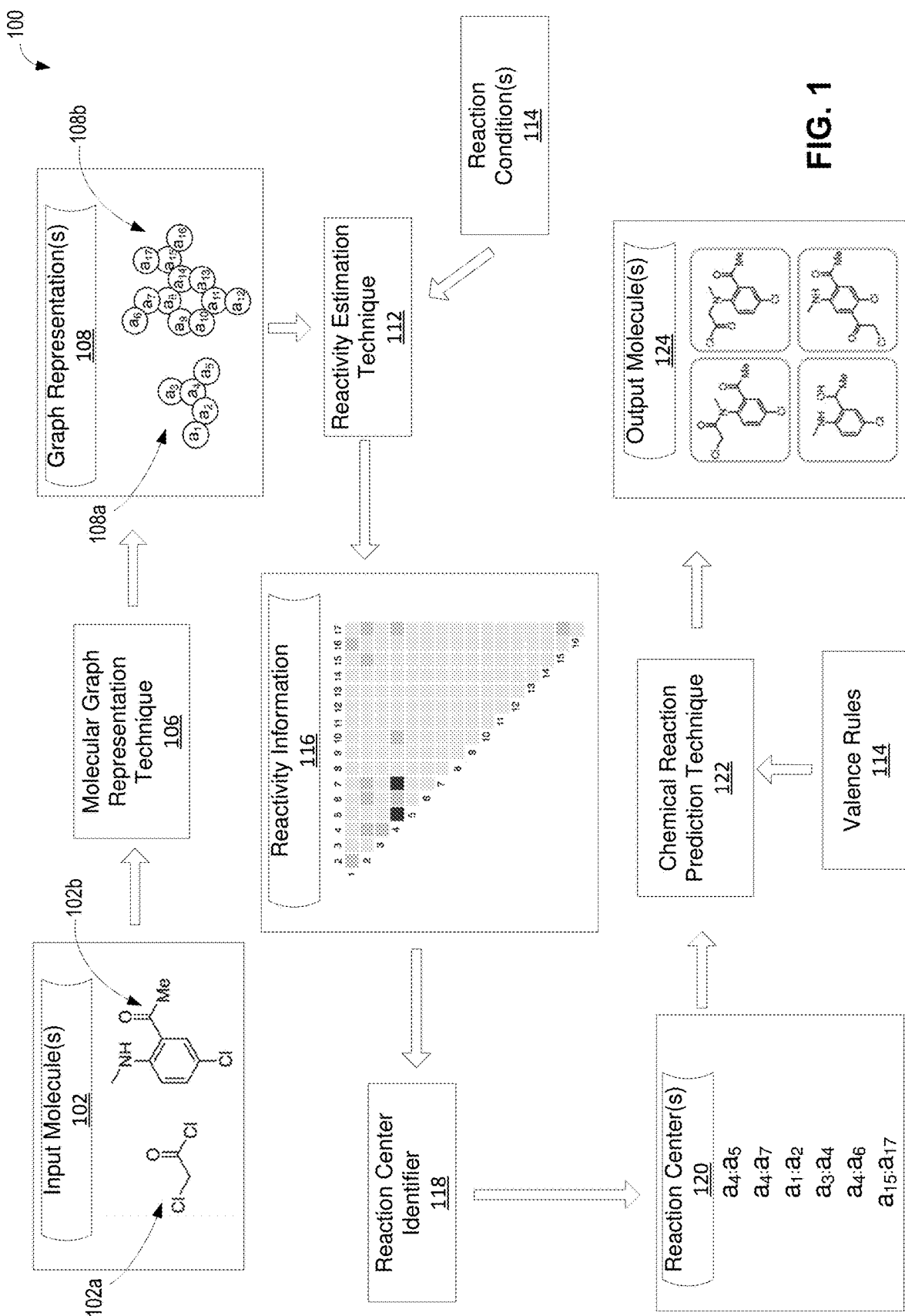
FIG. 1 is a diagram of an illustrative input molecule(s) data processing pipeline for predicting chemical reaction(s) based on identifying reaction centers(s), in accordance with some embodiments of the technology described herein.

Computational techniques that incorporate existing knowledge of chemical reactions may aid in predicting chemical reactions. However, the inventors have recognized that conventional computational techniques for predicting chemical reactions have limitations in correctly identifying atoms of a reactant molecule that is transformed by a chemical reaction. Furthermore, the inventors have recognized that conventional computational techniques may be improved upon because they are computationally expensive.

For example, some conventional techniques for predicting chemical reactions involve using submolecular patterns, also referred to as "reaction templates," that can be applied to a set of reactant molecules. Individual reaction templates indicate the type of chemical transformation (e.g., breaking of chemical bonds, formation of chemical bonds) that occurs for the reaction template. A reaction template that matches the set of reactants may indicate the type of reaction that occurs for the set of reactants and the products that form as an outcome of the reaction. These computational techniques that implement reaction templates have limitations because a chemical reaction is only identified if its corresponding reaction template is encoded. In addition, scaling these reaction template-based computational approaches becomes difficult because large amounts of data associated with the reaction templates must be encoded, which may increase computational costs associated with implementing these approaches because a large number of reaction templates are examined to identify a reaction template that matches a reactant.

In addition, some conventional techniques for predicting chemical reactions involve identifying individual mechanistic steps by analyzing electron movements (e.g. electron flow from an electron source to an electron sink) within molecular structures. To predict the products resulting from a chemical reaction for a set of reactants, these computational techniques are applied at each mechanistic step of the chemical reaction to identify individual intermediate molecular structures. Over multiple mechanistic steps, these computational techniques may become prohibitively computationally expensive, which may limit the feasibility of implementing these techniques to predict complex chemical reactions, such as chemical reactions with many mechanistic steps.

Accordingly, the inventors have developed new computational techniques for predicting chemical reactions, which do not involve matching reaction templates to reactants and do not require identifying individual mechanistic steps. Rather the new computational techniques involve identifying a reaction center, which is a set of atoms and bonds associated with the set of atoms that undergo a transformation between reactants and products during a chemical reaction. In some instances, a subset of the atoms (e.g., less than 10%, approximately 6%) in the reactants may participate in a particular chemical reaction. The inventors have recognized and appreciated that identifying the subset of atoms that participate in a chemical reaction as belonging to a reaction center may reduce the number of possible chemical transformations to analyze, which may decrease computational costs associated with predicting a chemical reaction.

The inventors have further recognized and appreciated that the subset of atoms that participate in a chemical reaction and belong in a reaction center may depend not only on properties of the atoms in the subset, but also on properties of atoms outside the subset. For example, the presence of a reagent molecule may be needed in order for a particular chemical reaction to proceed and identifying a subset of atoms as a reaction center may be based on whether the reagent is specified as a condition of the reaction. As another example, one or more atoms of a reactant molecule may contribute to steric effects during the chemical reaction such that another atom of the reactant molecule is likely to participate in a chemical reaction and may be identified as belonging to a reaction center. Accordingly, some embodiments of the technology described herein are directed to techniques for identifying a reaction center based on properties of atoms outside of the reaction center, including properties of atoms on the same molecule, on another molecule, and on a reagent molecule. These techniques developed by the inventors for identifying a reaction center may account for properties of atoms distal from atom(s) belonging in the reaction center, which may allow for more accurate reaction center identification, including identification of new reaction centers that may not yet exist as a reaction template and, thus, could not be identified using conventional computational techniques.

Some embodiments described herein address all of the above-described issues that the inventors have recognized with predicting chemical reactions. However, not every embodiment described herein addresses every one of these issues, and some embodiments may not address any of them. As such, it should be appreciated that embodiments of the technology described herein are not limited to addressing all or any of the above-discussed issues with predicting chemical reactions.

Some embodiments involve obtaining input molecule information identifying input molecule(s), predicting a chemical reaction that includes a transformation between the input molecule(s) and output molecule(s), and outputting information indicating the output molecule(s). The techniques described herein may be applied in predicting forward chemical reactions, where the set of product(s) produced from particular reactant(s) is identified. Accordingly, some embodiments involve obtaining input molecule information identifying input molecule(s) as reactant(s), predicting a forward chemical reaction that includes a transformation of the reactant(s) into product(s), and outputting information indicating the product(s). Such an approach may allow for predicting a set of products of a chemical reaction with a particular set of reactants. The techniques described herein may also be applied in predicting reverse chemical reactions (e.g., retrosynthetic chemical reactions), where the set of reactants used to produce a particular set of products is identified. Accordingly, some embodiments involve obtaining input molecule information identifying input molecule(s) as product(s), predicting a reverse chemical reaction that includes a transformation of product(s) into the reactant(s), and outputting information indicating the reactant(s). Such an approach may allow for predicting a set of reactants used to generate a particular set of a products, which may be used in chemical reaction design of a target molecule (e.g., drug molecule candidate) to identify possible synthetic pathways for producing the target molecule.

Regardless of the directionality of the chemical reaction, predicting the chemical reaction, according to some embodiments, may involve using the input molecule information and a statistical model relating properties of atoms outside a region of a molecule to reactivity of the molecule at the region to identify a set of reaction centers where the chemical reaction includes a transformation by modifying the input molecule(s) at the set of reaction center(s) to form the output molecule(s). Some embodiments may involve identifying a set of reaction center(s) in the input molecule(s) by using a statistical model relating properties of atoms proximate to an atom and properties of atoms distal to the atom to reactivity of the atom. In some embodiments, a reaction center may identify a set of atoms in the input molecule(s) that undergo a transformation in a chemical reaction. A reaction center may identify a set of atoms (e.g., a pair of atoms, a trio of atoms, etc.) in the input molecules. In some embodiments, a reaction center may include two or more atoms of the same input molecule that are separated by one or more atoms that do not participate in the chemical reaction. In some embodiments, a reaction center may include two or more atoms that are on different input molecules. A reaction center may identify a type of chemical interaction between a pair of atoms in the set of atoms. The type of chemical interaction may include a type of chemical bond between a pair of atoms, including a single covalent bond, a double covalent bond, and a triple covalent bond, as well as an indication of absence of a bond between a pair of atoms. In some embodiments, a reaction center may identify an electrostatic interaction between a pair of atoms.

In some embodiments, the statistical model may include parameters representing reactivity information for different pairs of atoms in the input molecule(s). The parameters representing reactivity information for different pairs of atoms in the input molecule(s) may include parameters representing reactivity information for different pairs of atoms in the input molecule(s) that are separated by one or more atoms in the same molecule. In some embodiments, the parameters representing reactivity information for different pairs of atoms in the input molecule(s) may include parameters representing reactivity information for different pairs of atoms that are on two different molecules. In some embodiments, the parameters representing reactivity information for different pairs of atoms in the input molecule(s) may include parameters representing reactivity information for pairs of neighboring atoms in the input molecule(s).

In some embodiments, identifying a reaction center includes estimating, using the input molecule information and the statistical model, reactivity information for atoms in the input molecule(s). The reactivity information may include reactivity values associated with sets of two or more atoms in the input molecule(s). Identifying the reaction center may involve using the reactivity values. In some embodiments, identifying the reaction center may include identifying a subset of the sets of atoms in the input molecule(s) as having a reactivity value above a threshold value, and identifying the subset in the input molecule(s) as the reaction center. Some embodiments involve ranking the sets of atoms in the input molecule(s) based on the reactivity values and identifying, based on the ranking, a subset of the sets of atoms as a reaction center.

Some embodiments involve predicting a chemical reaction by using a set of conditions under which the chemical reaction occurs. The set of conditions may include temperature, pH, pressure, a type of solvent, a type of catalyst, a type of reagent, a type of buffer, a reaction time, and light irradiation.

Some embodiments involve identifying output molecule(s) based on the predicted chemical reaction. In some embodiments, predicting a chemical reaction may include identifying one or more chemical bond changes for the reaction center(s) that complies with valence electron rules, determining a set of candidate output molecules based on transforming the input molecule(s) in accordance with the one or more chemical bond changes, and identifying, from the set of candidate output molecules, the output molecule(s).

Some embodiments involve scoring the output molecule(s), which may allow for an indication of one or more output molecules as a likely outcome of a chemical reaction that includes the input molecule(s). Some embodiments include assigning a score to each output molecule, selecting one or more output molecules as having a likelihood of being part of a chemical reaction that includes the input molecule(s) based on the scores, and outputting an indication of the selected one or more output molecules. In some embodiments, assigning the scores to the output molecules is performed by comparing each output molecule to the input molecule(s). In some embodiments, assigning the scores to the output molecules is performed by identifying values representing chemical differences between atoms in a set of output molecules to the corresponding atoms in the input molecule(s), and determining a score based on the values.

The format of the input molecule information may include a molecular graph representation of the input molecule(s). A molecular graph representation may include values associated with each atom in the input molecule(s). The values associated with an atom in the input molecule(s) may represent a chemical environment surrounding the atom. In some embodiments, the values associated with an atom may indicate a likelihood of the atom to react under a set of conditions (e.g., temperature, pH, pressure). In some embodiments, the values associated with an atom may indicate chemical properties (e.g., electronegativity, partial charge, orbital energies) of the atom. In some embodiments, the values associated with an atom may indicate structural information (e.g., atomic number, atomic mass, aromaticity, ring membership, chirality) corresponding to the atom. In some embodiments, a molecular graph representation may include nodes associated with individual atoms in the input molecule(s) and edges associated with bonds between pairs of atoms in the input molecule(s). Some embodiments involve obtaining a molecular graph representation of input molecule(s) by receiving an initial molecular graph representation and determining, based on the initial molecular graph representation, node labels corresponding to the nodes. A node label may correspond to an atom in the input molecule(s) and include values associated with the atom. In some embodiments, determining the node labels may be performed by modifying a node label associated with a node based on information stored in a node label of a neighboring node.

It should be appreciated that the various aspects and embodiments described herein be used individually, all together, or in any combination of two or more, as the technology described herein is not limited in this respect.

FIG. 1 is a diagram of an illustrative processing pipeline 100 for predicting chemical reactions, which may include obtaining input molecule(s) and using a statistical model relating properties of atoms outside a region of a molecule to reactivity of the molecule at the region to identify reaction center(s) of the input molecule(s), in accordance with some embodiments of the technology described herein. As shown in FIG. 1, input molecule(s) 102 may be obtained and analyzed using pipeline 100. In some embodiments, input molecule(s) 102 may identify a set of reactants and analysis of input molecule(s) 102 may include predicting a forward chemical reaction that includes the set of reactants, which may include identifying output molecule(s) 124 as a set of possible products included in the forward reaction. As shown in FIG. 1, input molecule(s) 102 includes input molecule 102a and input molecule 102b and output molecule(s) 124 identified by pipeline 100. Output molecule(s) 124 may identify possible products generated as an outcome of a forward chemical reaction that includes input molecule 102a and input molecule 102b as reactants. In other embodiments, input molecule(s) 102 may identify one or more products and analysis of input molecule(s) 102 may include predicting a reverse chemical reaction, which may include identifying output molecule(s) 124 as a set of reactants that may produce input molecule(s) 102.

Some embodiments may involve generating input molecule information identifying input molecule(s) 102. The input molecule information may include generating a molecular graph representation(s) 108 of input molecule(s) 102. As shown in FIG. 1, molecular graph representation 108a corresponds to input molecule 102a and molecular graph representation 108b corresponds to input molecule 102b. A molecular graph representation of a molecule may include nodes corresponding to atoms in the molecule and edges corresponding to bonds between pairs of atoms. For example, nodes $a_1$ and $a_5$ in molecular graph representation 108a correspond to the chlorine atoms in input molecule 102a. As another example, node $a_{17}$ in molecular graph representation 108b corresponds to the oxygen atom in input molecule 102b. In some embodiments, a node may correspond to multiple atoms in a molecule, such as a functional group (e.g., methyl, thiol, amine, alcohol) of a molecule. For example, node $a_{16}$ in molecular graph representation 108b corresponds to the methyl group (referenced as "Me") in input molecule 102b.

Molecular graph representation technique 106 may be used to generate molecular graph representation(s) 108 for a set of input molecule(s) 102. Molecular graph representation technique 106 may include generating values associated with individual atoms of input molecule(s) 102 that indicate characteristics of the atom, including a likelihood of the atom to react under a set of conditions (e.g., temperature, pH, pressure), a chemical property (e.g., electronegativity, partial charge, orbital energies) of the atom, structural information (e.g., atomic number, atomic mass, aromaticity, ring membership, chirality) of the atom. Molecular graph representation technique 106 may generate values associated with an atom as a node label for the node corresponding to the atom. In some embodiments, a node label for a node in a molecular graph representation may include a vector that includes values associated with atom represented by the node. The values associated with an atom may identify the local chemical environment of the atom. In some embodiments, molecular graph representation technique 106 may generate molecular graph representation(s) 108 through a process that modifies node labels to account for information in node labels of neighboring nodes. The resulting modified node labels may provide an indication of not only characteristics of individual atoms associated with the node labels but also properties of neighboring atoms. In some embodiments, molecular graph representation technique 106 may include applying an attention model to the node labels, which may include modifying an individual node label with a weighted combination of some or all of the other node labels in a molecular graph representation. In modifying a particular node label, the weights used for other node labels may quantify the relative perceived importance of those other node labels on the particular node label.

In some embodiments, molecular graph representation technique 106 may perform multiple iterations of a node label modification process to generate molecular graph representation(s) 108 of input molecule(s) 102. Over multiple iterations of relabeling the node labels to include information in neighboring node labels, the resulting modified node labels include information associated with not only a particular atom and its neighboring atom(s), but also other atoms in input molecule(s) 102. The resulting node label for a particular node generated by molecular graph representation technique 106 may include the values associated with the atom that correspond to the node. The values associated with the atom may provide an indication of how likely the atom is to react under a set of conditions. One type of value associated with an atom may indicate whether the atom associated with the node label is electron rich. If the atom is identified as being electron rich, then the atom may be indicated as a possible electron source when predicting a chemical reaction using input molecule(s) 102. Another type of value associated with an atom may indicate whether the atom associated with the node label is electron poor. In a case where the atom is identified as being electron poor, then the atom may be indicated as a possible electron sink when predicting a chemical reaction using input molecule(s) 102. Yet, another type of value associated with an atom may indicate the atom as belonging to a functional group that may act as a leaving group during a chemical reaction.

Molecular graph representation technique 106 may generate graph representation(s) 108 by implementing an isomorphism test (e.g., Weisfeiler-Lehman isomorphism test). Additional discussion for how molecular graph representations are generated is described herein including in Section A.3.1.1.

It should be appreciated that input molecule information identifying input molecule(s) 102 may have formats other than a molecular graph representation as techniques for predicting chemical reactions and identifying output molecule(s) 124 are not limited by the format of the input molecule information.

Regardless of the format of the input molecule information identifying input molecule(s) 102, reactivity estimation technique 112 may receive the input molecule information and use the input molecule information to estimate reactivity information 116. Reactivity estimation technique 112 may include estimating reactivity information 116 by estimating parameters of a statistical model representing reactivity information for multiple atoms in input molecule(s) 102. In some embodiments, a parameter of the statistical model may correspond to an interaction between multiple atoms, and estimating reactivity information may include estimating a value for the parameter. The estimated value for the parameter may indicate a degree of reactivity between the multiple atoms. As shown in FIG. 1, reactivity information 116 may include estimated values associated with one or more chemical interactions of different pairs of atoms in input molecule(s) 102. In the exemplary reactivity information shown in FIG. 1, each square is associated with two atoms, which are identified by the node labels in the molecular graph representation 108 of the input molecule(s), and the grayscale associated with each square identifies the relative value of a parameter of the statistical model that corresponds to an interaction between the two identified atoms. Higher values (indicated by darker shades) correspond to a higher degree of pairwise atom interaction in comparison to lower values (indicated by lighter shades).

Although FIG. 1 shows reactivity information 116 having a single value for each atom pair, where the value is represented by the grayscale associated with the square for is corresponding atom pair, it should be appreciated that reactivity information 116 may include multiple values for one or more atom pairs, where the individual values may correspond to particular types of chemical interactions between atoms in a pair (e.g., a type of bond, a type of electrostatic interaction). For example, reactivity information 116 for one pair of atoms may include a first value corresponding to the two atoms interacting via a single bond, a second value corresponding to the two atoms interacting via a double bond, and a third value corresponding to the two atoms interacting via an electrostatic interaction. In some embodiments, reactivity information 116 may include multiple values for each pair of atoms with each value corresponding to a different type of chemical interaction between the atoms in the pair.

It should be appreciated that the statistical model may include parameters representing interactions between different categories of sets of atoms in input molecule(s) 102. In some embodiments, the statistical model may include parameters representing reactivity information for different pairs of atoms in the same input molecule. As an example, atoms identified by node labels $a_4$ and $a_5$ corresponding to a carbon atom and a chlorine atom in input molecule 102a, respectively, have a higher value estimated by reaction estimation technique 112 than atoms identified by node labels $a_4$ and $a_1$, which corresponds to a different chlorine atom in input molecule 102a. In some embodiments, the statistical model may include parameters representing reactivity information for different pairs of atoms in the same input molecule that are separated by one or more atoms in the input molecule. For example, reactivity information 116 includes a value indicating reactivity between atoms identified by node labels $a_{13}$ and $a_7$ corresponding to a chlorine atom and a carbon atom in input molecule 102a, respectively, and are separated by atoms identified by node labels $a_8$, $a_9$, $a_{10}$, $a_{11}$, and $a_{12}$, which correspond to carbon atoms in input molecule 102b. In some embodiments, the statistical model may include parameters representing reactivity information between two or more atoms that are on different input molecules. The reactivity information 116 shown in FIG. 1 includes values corresponding to pairwise interactions between an atom of input molecule 102a and an atom of input molecule 102b. As an example, a carbon atom in input molecule 102a identified by node label $a_4$ and a nitrogen atom on input molecule 102b identified by node label $a_7$ have a high value estimated by reactivity estimation technique 112.

In some embodiments, estimating reactivity information 116 may include using reaction condition(s) 114, which may describe conditions under which a reaction that includes input molecule(s) 102 occurs. Examples of reaction condition(s) 114 that may be used by reactivity estimation technique 112 include temperature, pH, pressure, a type of solvent, a type of catalyst, a type of reagent, a type of buffer, a reaction time for the chemical reaction, and light irradiation on input molecule(s). In some embodiments, information identifying input molecule(s) 102 may include information identifying reaction condition(s) 114. Reaction condition(s) 114 may include information identifying a structure of a particular molecule (e.g., reagent, catalyst, solvent). In such cases, input molecule(s) 102 may identify the particular molecular structure as part of reaction condition(s) 114. Reactivity estimation technique 112 may estimate reactivity information 116 by estimating values for parameters of the statistical model based on the reaction condition(s) 114. For example, a degree of reactivity between multiple atoms may depend on the presence of a particular reagent during a chemical reaction. If reaction condition(s) 114 indicate the reagent as being present, then a value for a parameter representing reactivity between the atoms may be estimated to be higher than if reaction condition(s) 114 indicate the reagent as not being present. As another example, reactivity between two atoms may be more likely to occur in the presence of a high pH than in the presence of a low pH. If reaction condition(s) 114 indicate that the pH is low, then a value for a parameter representing reactivity between the two atoms may be estimated to be lower than if the pH is high.

Estimating reactivity information 116 may include determining values of parameters corresponding to interactions between multiple atoms in input molecule(s) using the input molecule information. In embodiments that include using a molecular graph representation of the input molecules, reactivity estimation technique 112 may use the information stored in node labels of the molecular graph representation in estimating the values of the parameters.

Estimating the reactivity information may include determining values for parameters of the statistical model using any suitable computational method(s). In some embodiments, the estimation may be performed by using a neural network algorithm, which may implement one or more functions including a sigmoid function, a softmax non-linearity function, a rectified linear unit, random forests, and gradient boosted random forest. Additional discussion for how reactivity information is generated is described herein including in Section A.3.1.2.

Reaction center identifier 118 may identify reaction center(s) 120 using reactivity information 116 estimated by reactivity estimation technique 112. Reaction center identifier 118 may identify reaction center(s) 120 using the estimated values of parameters in the one or more statistical models that may be included in reaction center identifier 118 as described herein. Some embodiments involve identifying reaction center(s) 120 by identifying combinations of atoms in input molecule(s) 102 that have a higher degree of reactivity than other atom combinations. In some embodiments, reaction center identifier 118 may rank different atom combinations based on the estimated values and select a subset of the atom combinations as having a high ranking (e.g., highest ranking, the two highest rankings, three highest rankings, etc.). The selected subset of atom combinations may be identified as the reaction center(s). In some embodiments, reaction center identifier 118 may identify a set of atom combinations in input molecule(s) 102 as having a reactivity value above a threshold value. Other techniques may be used by reaction center identifier 118 to identify combinations of atoms in input molecule(s) as having particularly high reactivity values estimated by reactivity estimation technique 112. Some embodiments may identify pairs of atoms in input molecule(s) 102 that have a high estimated reactivity value as reaction center(s) 120. For example, reactivity information 116 shown in FIG. 1 includes a high reactivity value (indicated by the dark shade) for an interaction between atoms identified by node labels $a_4$ and $a_5$, and reaction center identifier 118 may identify these atoms as a reaction center.

A reaction center identified by reaction center identifier 118 may identify a set of atoms (e.g., a pair of atoms, a trio of atoms) in input molecule(s) 102 and one or more chemical interactions between pairs of atoms in the set of atoms. In some embodiments, a chemical interaction identified by a reaction center may include a type of bond (e.g., a single bond, a double bond, a triple bond). A chemical interaction identified by a reaction center may include an indication of absence of a bond between atoms included in the reaction center. In some embodiments, a reaction center may identify an electrostatic interaction between atoms included in the reaction center. In some embodiments, a reaction center identified by reaction center identifier 118 may include multiple values for a pair of atoms, where the individual values correspond to different possible types of chemical interactions between the pair of atoms.

Different combinations of atoms in input molecule(s) 102 may be identified as a reaction center. Reaction center identifier 118 may identify a set of atoms of the same input molecule as a reaction center, and in some embodiments, one or more types of chemical interactions between atoms in the set. For example, reaction center $a_4:a_5$ indicates a reaction center that includes two atoms of input molecule 102*a*. In some embodiments, reaction center identifier 118 may identify a reaction center as a set of atoms of the same input molecule where two atoms in the set of atoms are separated by one or more atoms that are outside of the reaction center. Although not included in the reaction center(s) 120 shown in FIG. 1, the two atoms of input molecule 102*b* associated with node labels $a_{10}$ and $a_{13}$ are separated by the atom associated with node label $a_{11}$ and would be an example of this type of reaction center if these two atoms were identified as a reaction center. In some embodiments, reaction center identifier 118 may identify a set of atoms that includes atoms of different input molecules as a reaction center. For example, reaction center $a_4:a_7$ indicates a reaction center that includes an atom of input molecule 102*a* and an atom of input molecule 102*b*. In some embodiments, reaction center identifier 118 may identify a set of atoms as a reaction center that includes a first pair of atoms where a bond between the two atoms is lost during a chemical reaction and a second pair of atoms where a bond forms between the two atoms during the chemical reaction. In some instances, an atom may belong in both the first pair and the second pair, which may indicate that the atom breaks a bond with one atom and forms a bond with another atom during the chemical reaction.

Chemical reaction prediction technique 122 may use reaction center(s) 120 to predict one or more chemical reactions that include input molecule(s) 102 and output molecule(s) 124. In embodiments where input molecule(s) 102 are reactant(s) of a chemical reaction, chemical reaction prediction technique 122 may predict one or more forward chemical reactions that include output molecule(s) 124 as product(s). In embodiments where input molecule(s) 102 are product(s) of a chemical reaction, chemical reaction prediction technique 122 may predict one or more reverse chemical reactions that include output molecule(s) 124 as reactant(s).

Chemical reaction prediction technique 122 may predict a chemical reaction by identifying one or more chemical bond changes for reaction center(s) 120 that complies with a set of valence rules 114 and determining a set of candidate output molecules 124 based on transforming input molecule(s) in accordance with the one or more bond changes identified for reaction center(s) 120. Valence rules 114 may indicate constraints on how atoms form bonds and include information on the number of neighboring atoms and the types of neighboring atoms that an atom may bond with. Valence rules 114 may include information on the number of valence electrons for different types of atoms and how atoms may form bonds to complete valence shells. Other types of constraints may be used by chemical reaction prediction technique 122 to predict a chemical reaction to restrict the possible predicted chemical reactions and/or output molecule(s). One type of constraint may include a bias that a reaction center is unlikely to result in disconnected components, which may be referred to as a connectivity constraint. Additional discussion for how reactivity information is generated is described herein including in Section A.3.2.

Some embodiments involve ranking output molecule candidates predicted by chemical reaction prediction technique 122 and selecting, from the output molecule candidates, a set of output molecule(s) 124 as having a high likelihood of being included in a chemical reaction that includes input molecule(s) 102. Ranking of output molecule candidates may include assigning scores to individual output molecules. Assigning a score to an output molecule candidate may include comparing the output molecule candidate to input molecule(s) 102 to identify chemical differences between individual atoms in the output molecule candidate and the corresponding atoms in input molecule(s) 102. In some embodiments, values representing changes in chemical differences for an atom between input molecule(s) 102 and an output molecule candidate may be determined and used in assigning a score for an output molecule candidate. In this manner, the resulting score for an output molecule candidate may reflect changes in chemical properties of the atom between an input molecule and the output molecule candidate and these changes in chemical properties of the atom may be reflected in the resulting score for the output molecule candidate. For example, chemical differences for an atom between input molecule(s) 102 and a first output molecule candidate may indicate a change in stability of the atom as a result of the chemical reaction. For a second output molecule candidate, chemical differences for the atom between input molecule(s) 102 and the second output molecule candidate may indicate that the atom has less of a change in stability than compared to the first output molecule candidate. The resulting scores for the first and second output molecule candidates may reflect these differences in stability changes that the atom undergoes during a predicted chemical reaction and a higher score may be assigned to the first output molecule candidate than the second output molecule candidate to reflect that the atom has a larger change in stability for a chemical reaction that includes the first output molecule candidate than a chemical reaction that includes the second output molecule candidate. Chemical reaction prediction technique 122 may output an indication of the first output molecule candidate as an output molecule that is likely included in a chemical reaction that also includes input molecule(s) 102.

Some embodiments involve ranking output molecule candidates using reactivity information 116, including values estimated by reactivity estimation technique 112. In embodiments where reactivity information 116 includes reactivity values corresponding to possible types of chemical interactions between atoms, the reactivity values may be used in assigning a score for the output molecule candidates. For example, an output molecule candidate predicted by chemical reaction prediction technique 122 using a subset of reaction center(s) 120 having high reactivity values may have a higher ranking than another output molecule candidate predicted by chemical reaction prediction technique 122 using a subset of reaction center(s) 120 having low reactivity values. In particular, the reactivity values may not only be used to determine one or more changes in chemical interactions (e.g., breaking a bond, forming a bond) between atoms, but also the likelihood of such a change occurs. For example, a reaction center for two atoms may have a first reactivity value corresponding to a first type of chemical interaction between the two atoms and a second reactivity value corresponding to a second type of chemical interaction between the two atoms. The relative value between the first and the second reactivity values may be used in determining scores used in ranking a first output molecule candidate resulting from the first type of chemical interaction and a second output molecule candidate resulting from the second type of chemical interaction. For example, if the first type of chemical interaction is a bond formed between the two atoms and the second type of chemical interaction is an electrostatic interaction between the two atoms and the first reactivity value is higher than the second reactivity value, then an output molecule generated by forming a bond between the two atoms may have a higher ranking score than an output molecule generated by having electrostatic interaction between the two atoms.

Some embodiments involve generating a molecular graph representation of an output molecule candidate and comparing it with a molecular graph representation of input molecule(s) 102 in a manner that allows for atom by atom comparison between the two molecular graph representations. In such embodiments, values included in node labels of the molecular graph representation of the output molecule candidate may be compared to values included in node labels of the molecular graph representation of input molecule(s) 102. In some embodiments, a difference molecular graph representation may be generated by calculating a difference in values for a node label in the molecular graph representation of the output molecule candidate and a node label in the molecular graph representation of input molecule(s) 102 associated with a particular atom. A score for the output molecule candidate may be determined based on these differences in values for node labels between the output molecule candidate and input molecule(s) across the atoms in input molecule(s) 102. In some embodiments, these differences in values may be summed across all atoms in input molecule(s) 102. Any suitable technique may be used to generate a molecular graph of output molecule(s) 124, including molecular graph representation technique 106 which is described above in the context of generating a molecular graph representation for input molecule(s) 102. Additional discussion for ranking of output molecules is described herein including in Section A.3.3.

Figure 2:
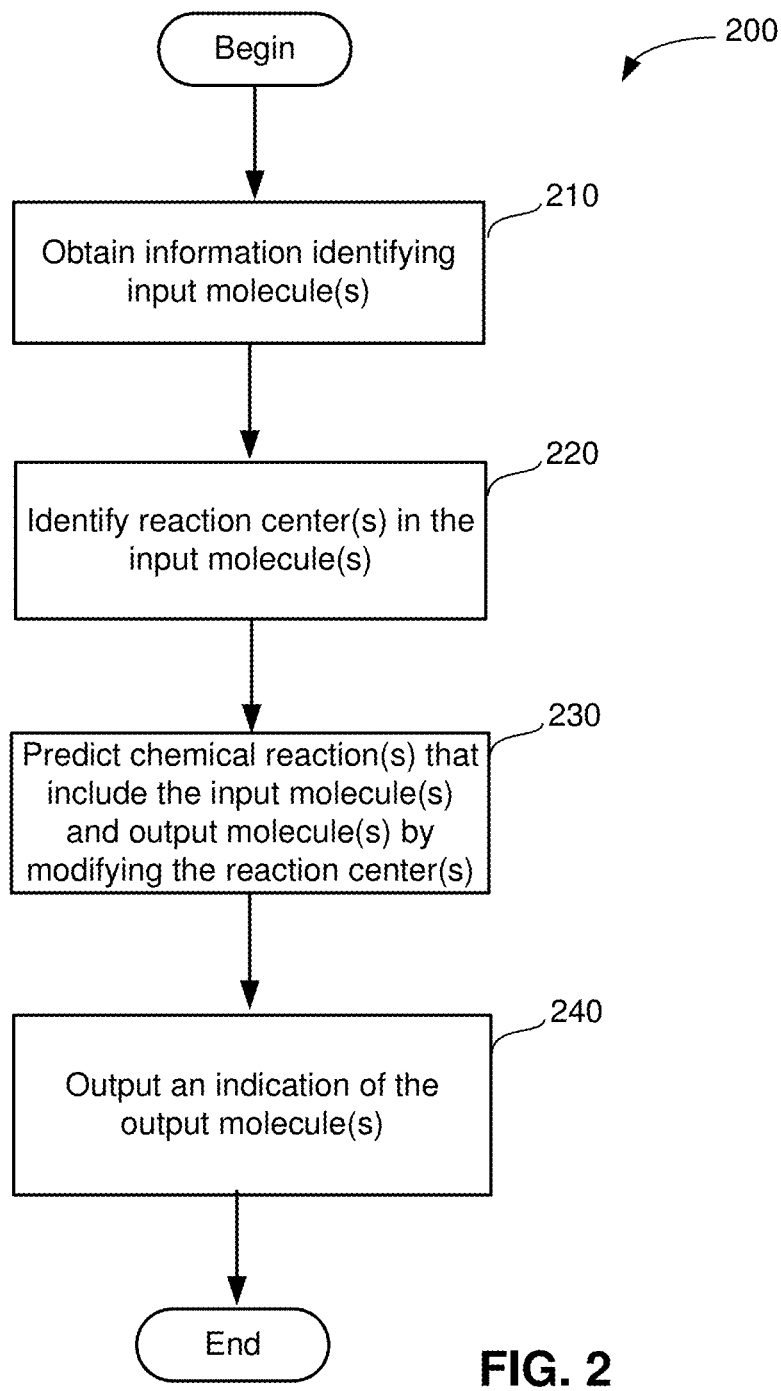
FIG. 2 is a flow chart of an illustrative process for predicting chemical reaction(s) and output molecule(s), using a statistical model that relates properties of atoms outside a region of a molecule to reactivity of the molecule at the region, and predicting chemical reaction(s) to identify reaction center(s) of input molecule(s), in accordance with some embodiments of the technology described herein.

FIG. 2 is a flow chart of an illustrative process 200 for predicting chemical reaction(s) and output molecule(s), using a statistical model that relates properties of atoms outside a region of a molecule to reactivity of the molecule at the region, and predicting chemical reaction(s) to identify reaction center(s) of input molecule(s), in accordance with some embodiments of the technology described herein. Process 200 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, reactivity estimation technique 112, reaction center identifier 118, and chemical reaction prediction technique 122 may perform some or all of process 200 to predict chemical reaction(s) and output molecule(s).

Process 200 begins at act 210, where information identifying input molecule(s) is obtained. In some embodiments, the input molecule(s) may identify reactant(s) of a forward chemical reaction being predicted. In other embodiments, the input molecule(s) may identify product(s) of a reverse chemical reaction being predicted.

Next, process 200 proceeds to act 220, where reaction center(s) are identified in the input molecule(s), such as by using reaction center identifier 118. The reaction center(s) may be identified using a statistical model relating properties of atoms outside a region of a molecule to reactivity of the molecule at the region to identify the reaction center(s). The statistical model may include parameters representing reactivity information for different pairs of atoms in the input molecule(s). A reaction center may identify a set of atoms in the input molecule(s) and a type of chemical interaction between pairs of atoms in the set of atoms. In some embodiments, a reaction center may identify a set of atoms in the input molecule(s) and a bond type between pairs of atoms in the set of atoms. The bond type identified in a reaction center may include the absence of a bond, a single bond, a double bond, a triple bond, and an aromatic bond. In some embodiments, a type of chemical interaction between pairs of atoms in a set of atoms may include absence of a bond, electrostatic interaction, or other types of atom interactions besides bond formation.

A reaction center may include a first atom and a second atom of an input molecule that are separated by one or more atoms of the input molecule that are outside the reaction center. In other words, the first atom and the second atom are separated by one or more atoms that are not included in the reaction center. In embodiments where there are multiple input molecules, a reaction center may include an atom of a first input molecule and a second atom of a second input molecule.

Next process 200 proceeds to act 230, where chemical reaction(s) are predicted, such as by using chemical reaction prediction technique 122. The chemical reaction(s) include the input molecule(s) and output molecule(s) generated by modifying the input molecule(s) at some or all of the identified reaction center(s). In some embodiments, predicting the chemical reaction(s) includes identifying chemical bond change(s) for the reaction center(s) in a manner that complies with a set of valence electron rules. A set of output molecules may be determined based on transforming the input molecule(s) in accordance with the identified chemical bond change(s).

In some embodiments, predicting the chemical reaction(s) may be performed by using a set of conditions under which a chemical reaction occurs, which may constrain the likelihood of some or all output molecules being formed. The set of conditions may include temperature, pH, pressure, a type of solvent, a type of catalyst, a type of reagent, a type of buffer, a reaction time, and light irradiation.

Next process 200 proceeds to act 240, where an indication of the output molecule(s) is output, such as to a user via a user interface. In embodiments where the input molecule(s) identify reactant(s) and a forward chemical reaction is predicted, output molecule(s) may identify possible product(s) that may form as a result of the predicted forward chemical reaction. Similarly, in embodiments, where input molecule(s) identify product(s) and a reverse chemical reaction is predicted, output molecule(s) may identify possible reactant(s) that may be used to form the product(s).

Figure 3:
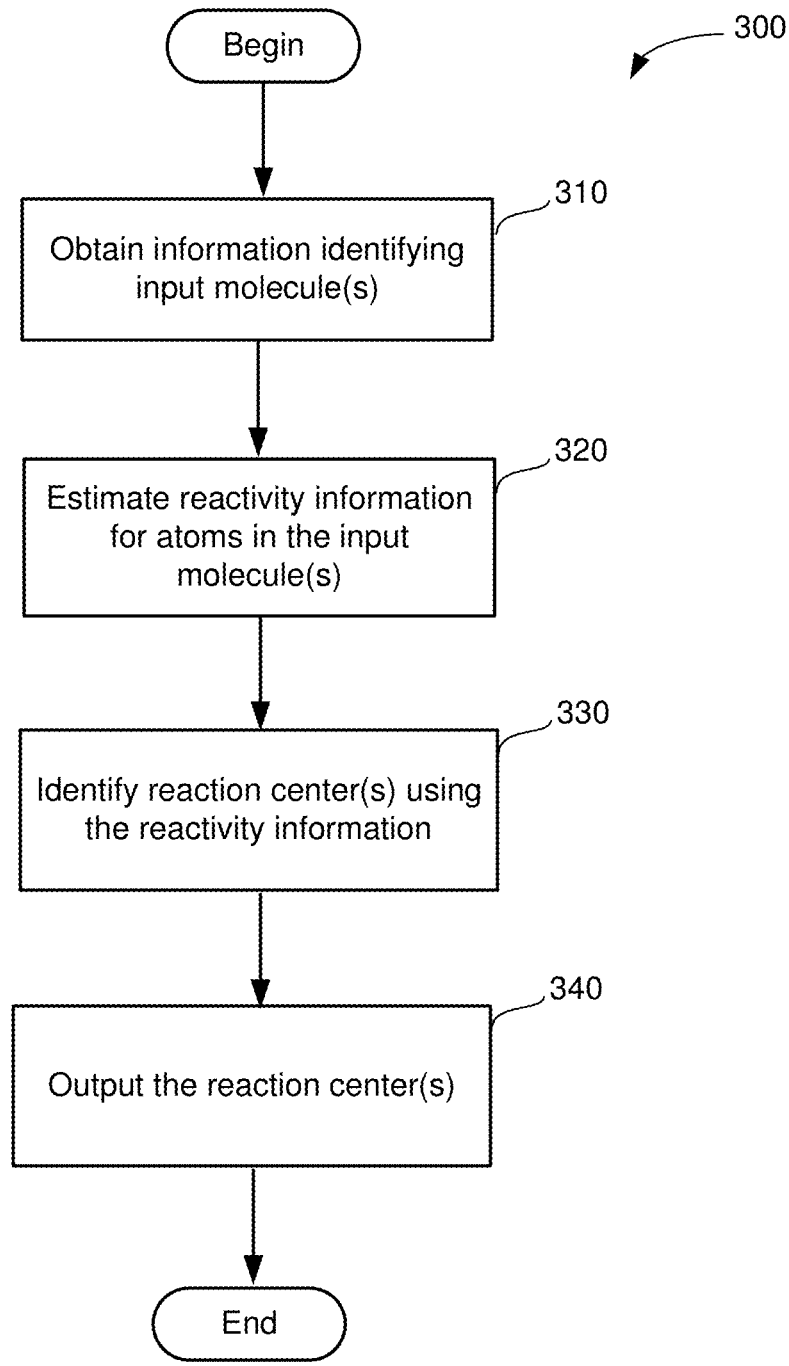
FIG. 3 is a flow chart of an illustrative process for identifying reaction center(s) in input molecule(s), using a statistical model that relates properties of atoms outside a region of a molecule to reactivity of the molecule at the region, in accordance with some embodiments of the technology described herein.

FIG. 3 is a flow chart of an illustrative process 300 for identifying reaction center(s) in input molecule(s), using a statistical model that relates properties of atoms outside a region of a molecule to reactivity of the molecule at the region, in accordance with some embodiments of the technology described herein. Process 300 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, reactivity estimation technique 112 and reaction center identifier 118 may perform some or all of process 300 to predict chemical reaction(s) and output molecule(s).

Process 300 begins at act 310, where information identifying input molecule(s) is obtained. The information identifying input molecule(s) may include a molecular graph representation of the input molecule(s), such as a molecular graph representation generated using molecular graph representation technique 106. Obtaining input molecule information may include obtaining a molecular graph representation of the input molecule(s). The molecular graph representation may include values associated with individual atoms in the input molecule(s). A node label corresponding to an atom in the input molecule(s) may include the values associated with the atom. The values associated with an atom may indicate a likelihood of the atom to react under a set of reaction conditions (e.g., pH, temperature, a type of reagent). In some embodiments, a value associated with an atom of an input molecule may indicate a chemical property of the atom. In some embodiments, a value associated with an atom of an input molecule may indicate structural information (e.g., atomic number, atomic mass) corresponding to the atom.

In some embodiments, obtaining a molecular graph representation of input molecule(s) may include receiving an initial molecular graph representation having nodes associated with individual atoms in the input molecule(s) and edges associated with bonds between pairs of atoms in the input molecule(s). Obtaining the molecular graph representation may further include determining, based on the initial molecular graph representation, node labels corresponding to the nodes. In some embodiments, determining the node labels is performed at least in part by modifying, for a node, the node label associated with the node based on information stored in node label(s) associated with neighboring node(s).

Next, process 300 proceeds to act 320, where reactivity information for atoms in the input molecule(s) is estimated, such as by using reactivity estimation technique 112. Estimating the reactivity information may include using the input molecule information and a statistical model to estimate the reactivity information, which may include reactivity values associated with sets of two or more atoms in the input molecule(s). The statistical model may include parameters representing reactivity information for different pairs of atoms in the input molecule(s). In some embodiments, the statistical model may include parameters representing reactivity information for different pairs of atoms in the input molecule(s) that are separated by one or more atoms in the same input molecule. In some embodiments, the statistical model may include parameters representing reactivity information for different pairs of atoms that are on two different input molecules. In some embodiments, the statistical model may include parameters representing reactivity information for pairs of neighboring atoms in an input molecule.

Next, process 300 proceeds to act 330, where reaction center(s) are identified in the input molecule(s) using the reactivity information, such as by using reaction center identifier 118. Reaction center(s) may be identified using the reactivity values. In some embodiments, identifying the reaction center(s) may include identifying a subset of atom combination sets in input molecule(s) as having a reactivity value above a threshold value, and identifying the subset of atom combination sets as the reaction center(s). In some embodiments, identifying the reaction center(s) may include ranking, based on the reactivity values, the atom combination sets in the input molecule(s). Using the ranking, a subset of the atom combination sets may be identified as the reaction center(s). In some embodiments, the subset of the atom combination sets identified as the reaction center(s) may have a high ranking and/or high reactivity values relative to the atom combination sets. An atom combination set may include two or more atoms in input molecule(s). Atoms in a combination set may include atoms on the same input molecule and/or atoms on different input molecules.

Next process 300 proceeds to act 340, where an indication of the reaction center(s) is output, such as to a user via a user interface. The indication of the reaction center(s) may identify the atoms included in the reaction center(s). For example, the indication of the reaction center(s) may include the node labels assigned to individual atoms in a molecular graph representation of the input molecule(s).

Figure 4:
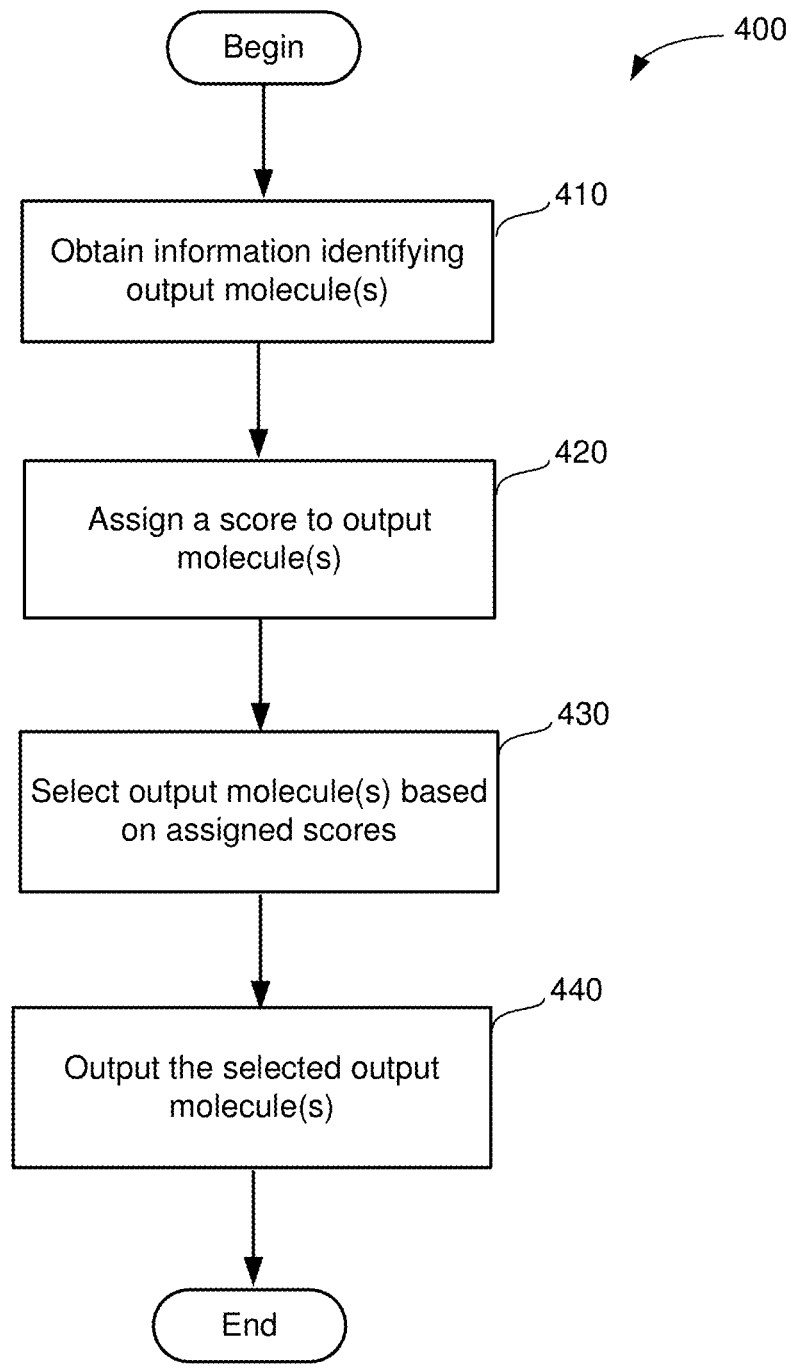
FIG. 4 is a flow chart of an illustrative process for selecting output molecule(s) as likely candidates, using scores assigned to each output molecule, in accordance with some embodiments of the technology described herein.

FIG. 4 is a flow chart of an illustrative process 400 for selecting output molecule(s) as likely candidates, using scores assigned to each output molecule(s), in accordance with some embodiments of the technology described herein. Process 400 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, chemical reaction prediction technique 122 may perform some or all of process 400 to predict chemical reaction(s) and output molecule(s).

Process 400 begins at act 410, where information identifying output molecule(s) is obtained. The information identifying the output molecule(s) may include a molecular graph representation of the output molecule(s), such as a molecular graph representation generated using molecular graph representation technique 106. Obtaining output molecule information may include obtaining a molecular graph representation of the output molecule(s). The molecular graph representation may include values associated with individual atoms in the output molecule(s). A node label corresponding to an atom in the output molecule(s) may include the values associated with the atom. The values associated with an atom may indicate a likelihood of the atom to react under a set of reaction conditions (e.g., pH, temperature, a type of reagent). In some embodiments, a value associated with an atom of an output molecule may indicate a chemical property of the atom. In some embodiments, a value associated with an atom of an output molecule may indicate structural information (e.g., atomic number, atomic mass) corresponding to the atom.

In some embodiments, obtaining a molecular graph representation of output molecule(s) may include receiving an initial molecular graph representation having nodes associated with individual atoms in the output molecule(s) and edges associated with bonds between pairs of atoms in the output molecule(s). Obtaining the molecular graph representation may further include determining, based on the initial molecular graph representation, node labels corresponding to the nodes. In some embodiments, determining the node labels is performed at least in part by modifying, for a node, the node label associated with the node based on information stored in node label(s) associated with neighboring node(s).

Next, process 400 proceeds to act 420, where a score is assigned to a set of output molecules, which may include one or more output molecules. For example, in embodiments where a set of multiple output molecules are predicted to result from a chemical reaction that includes the input molecule(s), act 420 may include assigning a score to the set of multiple output molecules rather than to individual output molecules in the set. Assigning a score to a set of output molecules may be performed by comparing the set of output molecules for a particular predicted chemical reaction to the input molecule(s). In some embodiments, assigning a score to a set of output molecules may include identifying values representing chemical differences between each atom in the output molecule in the set and the corresponding atom in the input molecule(s) and determining the score based on the values for the set of output molecules. In some embodiments, assigning a score to a set of output molecules may include using reactivity values corresponding to possible types of chemical interactions between atoms in the input molecule(s). In such embodiments, assigning a score to a set of output molecules may include determining the score based on the reactivity values corresponding to the types of chemical interactions involved in generating the set of output molecules.

Next, process 400 proceeds to act 430, where output molecule(s) are selected based on the assigned scores. In some embodiments, the output molecule(s) are selected as having a likelihood of being part of a chemical reaction that includes the input molecule(s). For example, output molecule(s) having high assigned scores (e.g., highest assigned score, two highest assigned scores, three highest assigned scores) may be selected.

Next process 400 proceeds to act 440, where an indication of the selected output molecule(s) is output, such as to a user via a user interface. In embodiments where the input molecule(s) identify reactant(s) and a forward chemical reaction is predicted, the selected output molecule(s) may identify the most likely product(s) that may form as a result of a forward chemical reaction that includes input molecule(s). Similarly, in embodiments, where input molecule(s) identify product(s) and a reverse chemical reaction is predicted, the selected output molecule(s) may identify the most likely reactant(s) that may be used to form the product(s).

Figure 5:
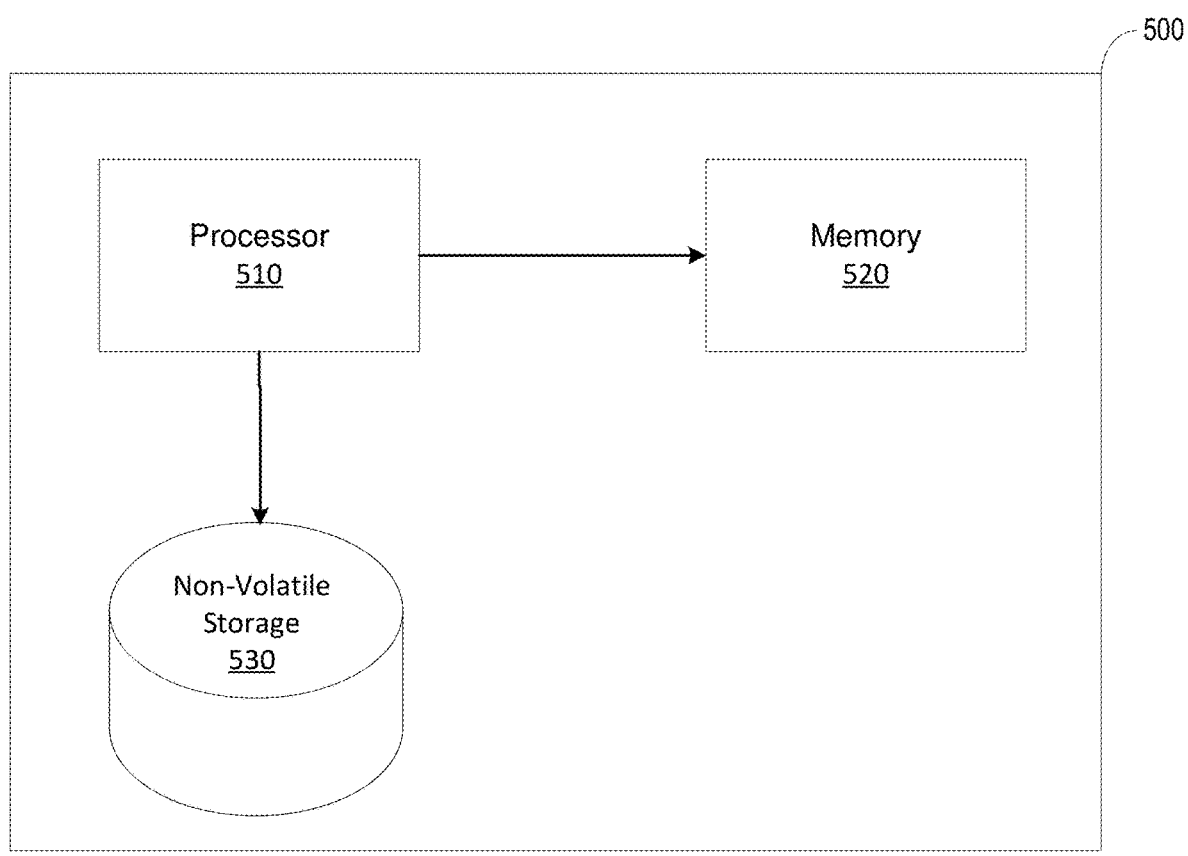
FIG. 5 is a block diagram of an illustrative computer system that may be used in implementing some embodiments of the technology described herein.

An illustrative implementation of a computer system 500 that may be used in connection with any of the embodiments of the technology described herein is shown in FIG. 5. The computer system 500 includes one or more processors 510 and one or more articles of manufacture that comprise non-transitory computer-readable storage media (e.g., memory 520 and one or more non-volatile storage media 530). The processor 510 may control writing data to and reading data from the memory 520 and the non-volatile storage device 530 in any suitable manner, as the aspects of the technology described herein are not limited in this respect. To perform any of the functionality described herein, the processor 510 may execute one or more processor-executable instructions stored in one or more non-transitory computer-readable storage media (e.g., the memory 520), which may serve as non-transitory computer-readable storage media storing processor-executable instructions for execution by the processor 510.

Some aspects of the technology described herein may be understood further based on the non-limiting illustrative embodiments described below in Section A. Any limitations of the embodiments described below in Section A are limitations only of the embodiments described in Section A, and are not limitations of any other embodiments described herein.

Section A

The prediction of organic reaction outcomes is a fundamental problem in computational chemistry. Since a reaction may involve hundreds of atoms, fully exploring the space of possible transformations is intractable. The current solution utilizes reaction templates to limit the space, but it suffers from coverage and efficiency issues. Techniques of the present application may implement a template-free approach to efficiently explore the space of product molecules by first pinpointing the reaction center—the set of nodes and edges where graph edits occur. Since only a small number of atoms contribute to reaction center, candidate products can be directly enumerated. The generated candidates are scored by a Weisfeiler-Lehman Difference Network that models high-order interactions between changes occurring at nodes across the molecule. Our framework outperforms the top-performing template-based approach with a 10% margin, while running orders of magnitude faster. Finally, we demonstrate that the model accuracy rivals the performance of domain experts.

1. Introduction

One of the fundamental problems in organic chemistry is the prediction of which products form as a result of a chemical reaction. While the products can be determined unambiguously for simple reactions, it is a major challenge for many complex organic reactions. Indeed, experimentation remains the primary manner in which reaction outcomes are analyzed. This is a time consuming, expensive, and requires the help of an experienced chemist. The empirical approach is particularly limiting for the goal of automatically designing efficient reaction sequences that produce specific target molecule(s), a problem known as chemical retrosynthesis.

Viewing molecules as labeled graphs over atoms, we propose to formulate the reaction prediction task as a graph transformation problem. A chemical reaction transforms input molecules (reactants) into new molecules (products) by performing a set of graph edits over reactant molecules, adding new edges and/or eliminating existing ones. Given that a typical reaction may involve more than 100 atoms, fully exploring all possible transformations is intractable. The computational challenge is how to reduce the space of possible edits effectively, and how to select the product from among the resulting candidates.

Figure 6:
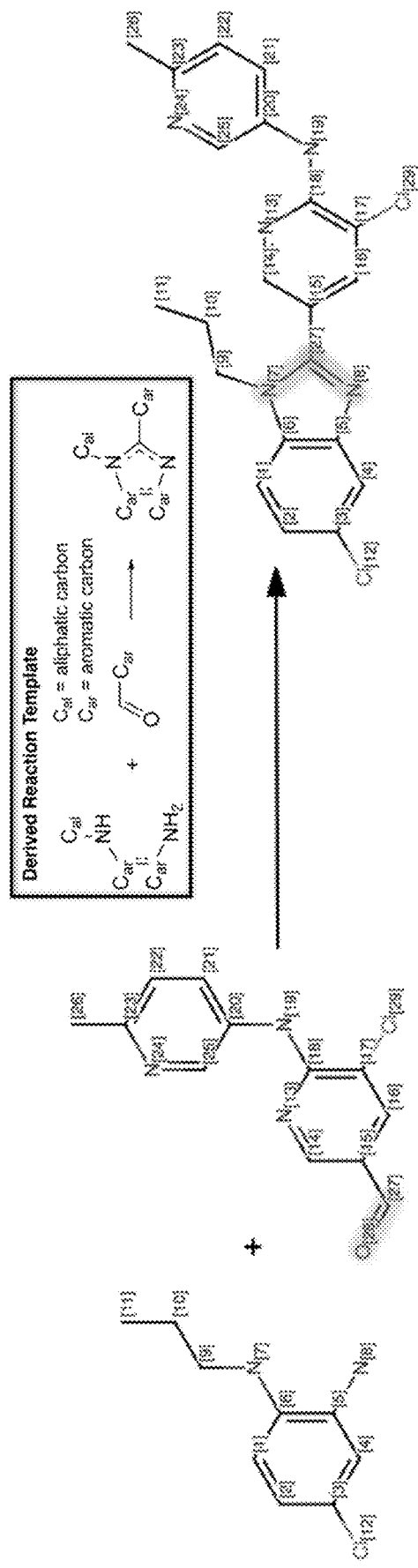
FIG. 6 is an example reaction where the reaction center is (27,28), (7,27), and (8,27), highlighted in green. Here bond (27,28) is deleted and (7,27) and (8,27) are connected by aromatic bonds to form a new ring. The corresponding reaction template consists of not only the reaction center, but nearby functional groups that explicitly specify the context.

The state-of-the art solution is based on reaction templates (FIG. 6). A reaction template specifies a molecular subgraph pattern to which it can be applied and the corresponding graph transformation. Since multiple templates can match a set of reactants, another model is trained to filter candidate products using standard supervised approaches. The key drawbacks of this approach are coverage and scalability. A large number of templates are required to ensure that at least one can reconstitute the correct product. The templates are currently either hand-crafted by experts or generated from reaction databases with heuristic algorithms. Beyond coverage, applying a template involves graph matching and this makes examining large numbers of templates prohibitively expensive. The current approach is therefore limited to small datasets with limited types of reactions.

We propose a template-free approach by learning to identify the reaction center, a small set of atoms/bonds that change from reactants to products. In our datasets, on average only 5.5% of the reactant molecules directly participate in the reaction. The small size of the reaction centers together with additional constraints on bond formations enables us to directly enumerate candidate products. Our forward-prediction approach is then divided into two key parts: (1) learning to identify reaction centers and (2) learning to rank the resulting enumerated candidate products.

Our technical approach builds on neural embedding of the Weisfeiler-Lehman isomorphism test. We incorporate a specific attention mechanism to identify reaction centers while leveraging distal chemical effects not accounted for in related convolutional representations. Moreover, we propose a novel Weisfeiler-Lehman Difference Network to learn to represent and efficiently rank candidate transformations between reactants and products.

We evaluate our method on two datasets derived from the USPTO, and compare our methods to the current top performing system. Our method achieves 83.9% and 77.9% accuracy on two datasets, outperforming the baseline approach by 10%, while running 140 times faster. Finally, we demonstrate that the model outperforms domain experts by a large margin.

2. Related Work

Template-Based Approach

Following traditional computer-assisted synthesis approaches, existing machine learning models for product prediction are built on reaction templates. These approaches differ in the way templates are specified and in the way the final product is selected from multiple candidates.

Molecular Graph Neural Networks

The question of molecular graph representation is a key issue in reaction modeling. In computational chemistry, molecules are often represented with Morgan Fingerprints, boolean vectors that reflect the presence of various substructures in a given molecule. Some techniques involve using a neural version of Morgan Fingerprints, where each convolution operation aggregates features of neighboring nodes as a replacement of the fixed hashing function.

3. Overview

Figure 7:
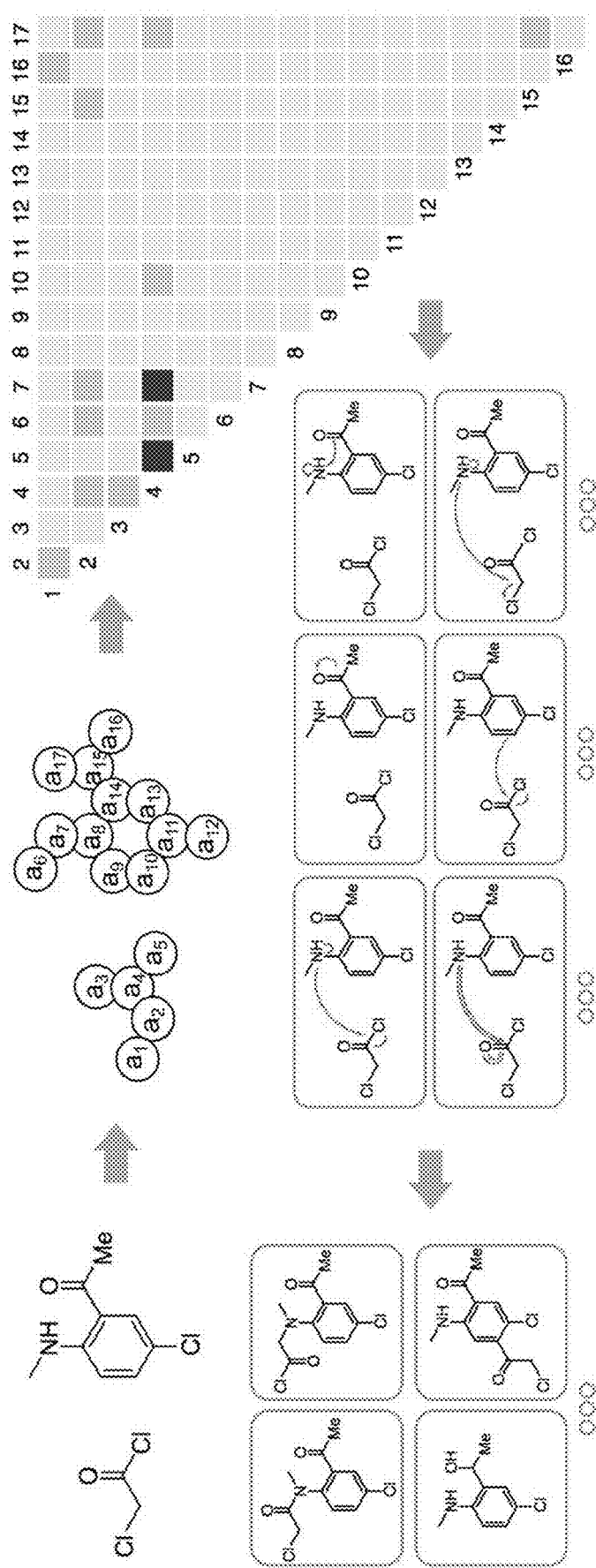
FIG. 7 is a schematic of an exemplary approach. (1) we train a model to identify pairwise atom interactions in the reaction center. (2) we pick the top K atom pairs and enumerate chemically-feasible bond configurations between these atoms. Each bond configuration generates a candidate outcome of the reaction. (3) Another model is trained to score these candidates to find the true product.

Our approach bypasses reaction templates by learning a reaction center identifier. Specifically, we train a neural network that operates on the reactant graph to predict a reactivity score for every pair of atoms (Section 3.1). A reaction center is then selected by picking a small number of atom pairs with the highest reactivity scores. After identifying the reaction center, we generate possible product candidates by enumerating possible bond configurations between atoms in the reaction center (Section 3.2) subject to chemical constraints. We train another neural network to rank these product candidates (represented as graphs, together with the reactants) so that the correct reaction outcome is ranked highest (Section 3.3). The overall pipeline is summarized in FIG. 7. Before describing the two modules in detail, we formally define some key concepts used throughout the paper.

Chemical Reaction

A chemical reaction is a pair of molecular graphs ($G_r$, $G_p$), where $G_r$ is called the reactants and $G_p$ the products. A molecular graph is described as G=(V, E), where V= $\{a_1, a_2, \ldots, a_n\}$ is the set of atoms and E=$\{b_1, b_2, \ldots, b_m\}$ is the set of associated bonds of varying types (single, double, aromatic, etc.). Note that $G_r$ has multiple connected components since there are multiple molecules comprising the reactants. The reactions used for training are atom-mapped so that each atom in the product graph has a unique corresponding atom in the reactants.

Reaction Center

A reaction center is a set of atom pairs $\{(a_i, a_j)\}$, where the bond type between $a_i$ and $a_j$ differs from $G_r$ to $G_p$. In other words, a reaction center is a minimal set of graph edits needed to transform reactants to products. Since the reported reactions in the training set are atom-mapped, reaction centers can be identified automatically given the product.

3.1 Reaction Center Identification

In a given reaction R=($G_r$, $G_p$), each atom pair ($a_u$, $a_v$) in $G_r$ is associated with a reactivity label $y_{uv} \in \{0, 1\}$ specifying whether their relation differs between reactants and products. The label is determined by comparing $G_r$ and $G_p$ with the help of atom-mapping. We predict the label on the basis of learned atom representations that incorporate contextual cues from the surrounding chemical environment. In particular, we build on a Weisfeiler-Lehman Network (WLN) that has shown superior results against other learned graph representations in the narrower setting of predicting chemical properties of individual molecules.

3.1.1 Weisfeiler-Lehman Network (WLN)

The WLN is inspired by the Weisfeiler-Lehman isomorphism test for labeled graphs. The architecture is designed to embed the computations inherent in WL isomorphism testing to generate learned isomorphism-invariant representations for atoms.

WL Isomorphism Test

The key idea of the isomorphism test is to repeatedly augment node labels by the sorted set of node labels of neighbor nodes and to compress these augmented labels into new, short labels. The initial labeling is the atom element. In each iteration, its label is augmented with the element labels of its neighbors. Such a multi-set label is compactly represented as a new label by a hash function. Let $c_v^{(L)}$ be the final label of atom $a_v$. The molecular graph G=(V, E) is represented as a set $\{(c_u^{(L)}, b_{uv}, c_v^{(L)})|(u, v) \in E\}$, where $b_{uv}$ is the bond type between u and v. Two graphs are said to be isomorphic if their set representations are the same. The number of distinct labels grows exponentially with the number of iterations L.

WL Network

The discrete relabeling process does not directly generalize to continuous feature vectors. Instead, we appeal to neural networks to continuously embed the computations inherent in the WL test. Let r be the analogous continuous relabeling function. Then a node $v \in G$ with neighbor nodes N(v), node features $f_v$, and edge features $f_{uv}$ is "relabeled" according to $$r(v) = \tau\left(U_1 f_v + U_2 \sum_{u \in N(v)} \tau(V[f_u, f_{uv}])\right) \quad (1)$$

where $\tau(\cdot)$ could be any non-linear function. We apply this relabeling operation iteratively to obtain context-dependent atom vectors $$h_v^{(l)} = \tau\left(U_1 h_v^{l-1} + U_2 \sum_{u \in N(v)} \tau(V[h_v^{l-1}, f_{uv}])\right) \quad (1 \le l \le L) \quad (2)$$

where $h_v^{(0)} = f_v$ and $U_1$, $U_2$, V are shared across layers. The final atom representations arise from mimicking the set comparison function in the WL isomorphism test, yielding $$c_v = \sum_{u \in N(v)} W^{(0)} h_u^{(L)} \odot W^{(1)} f_{uv} \odot W^{(2)} h_v^{(L)} \quad (3)$$

The set comparison here is realized by matching each rank-1 edge tensor $h_u^{(L)} \otimes f_{uv} \otimes h_v^{(L)}$ to a set of reference edges also cast as rank-1 tensors $W^{(0)}[k] \otimes M^{(1)}[k] \otimes W^{(2)}[k]$, where W[k] is the k-th row of matrix W. In other words, Eq. 3 above could be written as $$c_v[k] = \sum_{u \in N(v)} \langle W^{(0)}[k] \otimes W^{(1)}[k] \otimes W^{(2)}[k], h_u^{(L)} \otimes f_{uv} \otimes h_v^{(L)} \rangle \quad (4)$$

The resulting $c_v$ is a vector representation that captures the local chemical environment of the atom (through relabeling) and involves a comparison against a learned set of reference environments. The representation of the whole graph G is simply the sum over all the atom representations: $c_G = \Sigma_v c_v$.

3.1.2 Finding Reaction Centers with WLN

We present two models to predict reactivity: the local and global models. Our local model is based directly on the atom representations $c_u$ and $c_v$ in predicting label $y_{uv}$. The global model, on the other hand, selectively incorporates distal chemical effects with the goal of capturing the fact that atoms outside of the reaction center may be necessary for the reaction to occur. For example, the reaction center may be influenced by certain reagents (i.e., molecules that do not typically contribute atoms to the product but are nevertheless necessary for the reaction to proceed). We incorporate these distal effects into the global model through an attention mechanism.

Local Model

Let $c_u$, $c_v$ be the atom representations for atoms u and v, respectively, as returned by the WLN. We predict the reactivity score of (u, v) by passing these through another neural network:

$$s_{uv} = \sigma(u^T \tau(M_a c_u + M_a c_v + M_b b_{uv})) \quad (5)$$

where $\sigma(\cdot)$ is the sigmoid function, and $b_{uv}$ is an additional feature vector that encodes auxiliary information about the pair such as whether the two atoms are in different molecules or which type of bond connects them.

Global Model

Let $\alpha_{uv}$ be the attention score of atom v on atom u. The global context representation $\tilde{c}_u$ of atom u is calculated as the weighted sum of all reactant atoms where the weight comes from the attention module:

$$\tilde{c}_u = \sum_v \alpha_{uv} c_v; \quad \alpha_{uv} = \sigma(u^T \tau(P_a c_u + P_a c_v + P_b b_{uv})) \quad (6)$$

$$s_{uv} = \sigma(u^T \tau(M_a \tilde{c}_u + M_a \tilde{c}_v + M_b b_{uv})) \quad (7)$$

Note that the attention is obtained with sigmoid rather than softmax non-linearity since there may be multiple atoms relevant to a particular atom u.

Training

Both models are trained to minimize the following loss function:

$$\mathcal{L}(\mathcal{T}) = -\sum_{R \in \mathcal{T}} \sum_{u \neq v \in R} y_{uv} \log(s_{uv}) + (1 - y_{uv}) \log(1 - s_{uv}) \quad (8)$$

Here we predict each label independently because of the large number of variables. For a given reaction with N atoms, we need to predict the reactivity score of $O(N^2)$ pairs. This quadratic complexity prohibits us from adding higher-order dependencies between different pairs. Nonetheless, we found independent prediction yields sufficiently good performance.

3.2 Candidate Generation

We select the top K atom pairs with the highest predicted reactivity score and designate them, collectively, as the reaction center. The set of candidate products are then obtained by enumerating all possible bond configuration changes within the set. While the resulting set of candidate products is exponential in K, many can be ruled out by invoking additional constraints. For example, every atom has a maximum number of neighbors they can connect to (valence constraint). We also leverage the statistical bias that reaction centers are very unlikely to consist of disconnected components (connectivity constraint). Some multi-step reactions do exist that violate the connectivity constraint. As we will show, the set of candidates arising from this procedure is more compact than those arising from templates without sacrificing coverage.

3.3 Candidate Ranking

The training set for candidate ranking consists of lists $\mathcal{T} = \{(r, p_0, p_1, \bullet, p_m)\}$, where r are the reactants, $p_0$ is the known product, and $p_1, \bullet, p_m$ are other enumerated candidate products. The goal is to learn a scoring function that ranks the highest known product $p_0$. The challenge in ranking candidate products is again representational. We must learn to represent (r, p) in a manner that can focus on the key difference between the reactants r and products p while also incorporating the necessary chemical contexts surrounding the changes.

We again propose two alternative models to score each candidate pair (r, p). The first model naively represents a reaction by summing difference vectors of all atom representations obtained from a WLN on the associated connected components. Our second and improved model, called WLDN, takes into account higher order interactions between these differences vectors.

WLN with Sum-Pooling

Let $c_v^{(p_i)}$ be the learned atom representation of atom v in candidate product molecule $p_i$. We define difference vector $d_v^{(p_i)}$ pertaining to atom v as follows:

$$d_v^{(p_i)} = c_v^{(p_i)} - c_v^{(r)}; \quad s(p_i) = u^T \tau\left(M \sum_{v \in p_i} d_v^{(p_i)}\right) \quad (9)$$

Recall that the reactants and products are atom-mapped so we can use v to refer to the same atom. The pooling operation is a simple sum over these difference vectors, resulting in a single vector for each $(r, p_i)$ pair. This vector is then fed into another neural network to score the candidate product $p_i$.

Weisfeiler-Lehman Difference Network (WLDN)

Instead of simply summing all difference vectors, the WLDN operates on another graph called a difference graph. A difference graph $D(r, p_i)$ is defined as a molecular graph which has the same atoms and bonds as $p_i$, with atom v's feature vector replaced by $d_v^{(p_i)}$. Operating on the difference graph has several benefits. First, in $D(r, p_i)$, atom v's feature vector deviates from zero only if it is close to the reaction center, thus focusing the processing on the reaction center and its immediate context. Second, $D(r, p_i)$ explicates neighbor dependencies between difference vectors. The WLDN maps this graph-based representation into a fixed-length vector, by applying a separately parameterized WLN on top of $D(r, p_i)$:

$$h_v^{(p_i,l)} = \tau\left(U_1 h_v^{(p_i,l-1)} + U_2 \sum_{u \in N(v)} \tau(V[h_u^{(p_i,l-1)}, f_{uv}])\right) (1 \leq l \leq L) \quad (10)$$

$$d_v^{(p_i,L)} = \sum_{u \in N(v)} W^{(0)} h_u^{(p_i,L)} \odot W^{(1)} f_{uv} \odot W^{(2)} h_v^{(p_i,L)} \quad (11)$$

where $h_v^{(p_i,0)} = d_v^{(p_i)}$. The final score of $p_i$ is $s(p_i) = u^T \tau (M \Sigma_{v \in p_i} d_v^{(p_i,L)})$.

Training

Both models are trained to minimize the softmax log-likelihood objective over the scores $\{s(p_0), s(p_1), \ldots, s(p_m)\}$ where $s(p_0)$ corresponds to the target.

4. Experiments

Data As a source of data for our experiments, we used reactions from USPTO granted patents. After removing duplicates and erroneous reactions, we obtained a set of 480K reactions, to which we refer in the paper as USPTO. This dataset is divided into 400K, 40K, and 40K for training, development, and testing purposes.

In addition, for comparison purposes we report the results on the subset of 15K reaction from this dataset (referred as USPTO-15K). We use splits, with 10.5K, 1.5K, and 3K for training, development, and testing.

Setup for Reaction Center Identification

The output of this component consists of K atom pairs with the highest reactivity scores. We compute the coverage as the proportion of reactions where all atom pairs in the true reaction center are predicted by the model, i.e., where the recorded product is found in the model-generated candidate set.

The model features reflect basic chemical properties of atoms and bonds. Atom-level features include its elemental identity, degree of connectivity, number of attached hydrogen atoms, implicit valence, and aromaticity. Bond-level features include bond type (single, double, triple, or aromatic), whether it is conjugated, and whether the bond is part of a ring.

Both our local and global models are build upon a Weisfeiler-Lehman Network, with unrolled depth 3. All models are optimized with Adam, with learning rate decay factor 0.9.

Setup for Candidate Ranking

The goal of this evaluation is to determine whether the model can select the correct product from a set of candidates derived from a reaction center. We compare model accuracy against top-performing template-based approach. This approach employs frequency-based heuristics to construct reaction templates and then uses a neural model to rank the derived candidates. As explained above, due to the scalability issues associated with this baseline, we can only compare on USPTO-15K.

For all experiments, we set K=8 for candidate generation. This set-up achieves 90% and 92% coverage on two datasets and yields 250 candidates per reaction. In addition, we compare variants of our model on the full USPTO dataset. To compare a standard WLN representation against its counterpart with Difference Networks (WLDN), we train them under the same setup, fixing the number of parameters to 650K.

Finally, to factorize the coverage of candidate selection and the accuracy of candidate ranking, we consider two evaluation scenarios: (1) the candidate list as derived from reaction center; (2) the above candidate list augmented with the true product if not found. This latter setup is marked with (*).

TABLE 1a

Results on USPTO-15K and USPTO datasets. Reaction Center Prediction Performance. Coverage is reported by picking the top K (K = 6, 8, 10) reactivity pairs. |θ| is the number of model parameters.

| Method | \|θ\| | K = 6 | K = 8 | K = 10 |
|---|---|---|---|---|
| USPTO-15K | | | | |
| Local | 572K | 80.1 | 85.0 | 87.7 |
| Local | 1003K | 81.6 | 86.1 | 89.1 |
| Global | 756K | 86.7 | 90.1 | 92.2 |
| USPTO | | | | |
| Local | 572K | 83.0 | 87.2 | 89.6 |
| Local | 1003K | 82.4 | 86.7 | 89.1 |
| Global | 756K | 89.8 | 92.0 | 93.3 |
| Avg. Num. of Candidates (USPTO) | | | | |
| Template | — | | 482.3 out of 5006 | |
| Global | — | 60.9 | 246.5 | 1076 |

TABLE 1b

Results on USPTO-15K and USPTO datasets. Candidate Ranking Performance. Precision at ranks 1, 3, 5 are reported.

| Method | Cov. | P@1 | P@3 | P@5 |
|---|---|---|---|---|
| USPTO-15K | | | | |
| Template | 100.0 | 72.1 | 86.6 | 90.7 |
| WLN | 90.1 | 74.9 | 78.6 | 85.8 |
| WLDN | 90.1 | 76.9 | 81.3 | 86.8 |
| WLN(*) | 100.0 | 79.9 | 85.2 | 93.9 |
| WLDN(*) | 100.0 | 83.9 | 88.1 | 95.2 |
| USPTO | | | | |
| WLN | 92.0 | 73.8 | 83.4 | 87.0 |
| WLDN | 92.0 | 74.6 | 84.3 | 87.6 |
| WLN(*) | 100.0 | 76.8 | 88.9 | 93.6 |
| WLDN(*) | 100.0 | 77.9 | 92.5 | 96.9 |

(*)denotes that the true product was added if not covered by the previous stage.

4.1 Results
Reaction Center Identification

Table 1a reports the coverage of the model as compared to the real reaction core. Clearly, the coverage depends on the number of atom pairs K, with the higher coverage for larger values of K. These results demonstrate that even for K=8, the model achieves high coverage, above 90%.

The results also clearly demonstrate the advantage of the global model over the local one, which is consistent across all experiments. The superiority of the global model is in line with the well-known fact that reactivity depends on more than the immediate local environment surrounding the reaction center. The presence of certain functional groups (structural motifs that appear frequently in organic chemistry) far from the reaction center can promote or inhibit different modes of reactivity. Moreover, reactivity is often influenced by the presence of reagents, which are separate molecules that may not directly contribute atoms to the product. Consideration of both of these factors necessitates the use of a model that can account for long-range dependencies between atoms.

Figure 8:
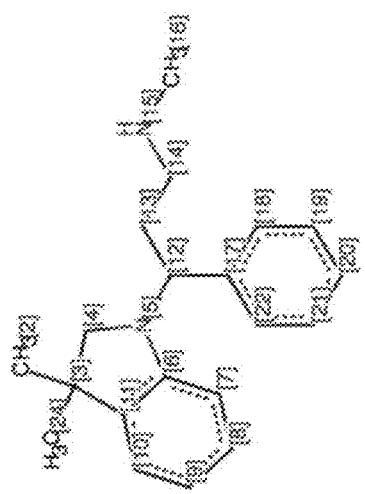
FIG. 8 is a schematic of an exemplary reaction that reduces the carbonyl carbon of an amide by removing bond 4-23 (dotted circle). Reactivity at this site would be highly unlikely without the presence of borohydride (atom 25, dashed circle). The global model correctly predicts bond 4-23 as the most susceptible to change, while the local model does not even include it in the top ten predictions. The attention map of the global model show that atoms 1, 25, and 26 were determinants of atom 4's predicted reactivity.
Figure 8:
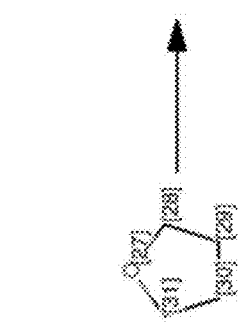
Figure 8:
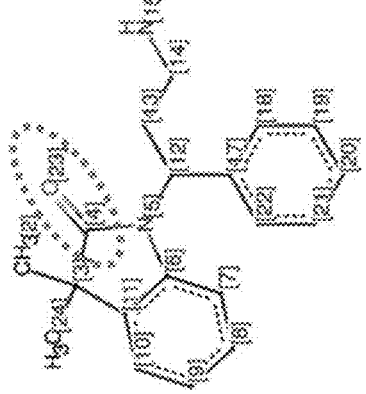
Figure 8:
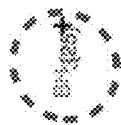

FIG. 8 depicts one such example, where the observed reactivity can be attributed to the presence of a reagent molecule that is completely disconnected from the reaction center itself. While the local model fails to anticipate this reactivity, the global one accurately predicts the reaction center. The attention map highlights the reagent molecule as the determinant context.

Candidate Generation

Here we compare the coverage of the generated candidates with the template-based model. Table 1a shows that for K=6, our model generates an average of 60.1 candidates and reaches a coverage of 89.8%. The template-based baseline requires 5006 templates extracted from the training data (corresponding to a minimum of five precedent reactions) to achieve 90.1% coverage with an average of 482 candidates per example.

Figure 9A:
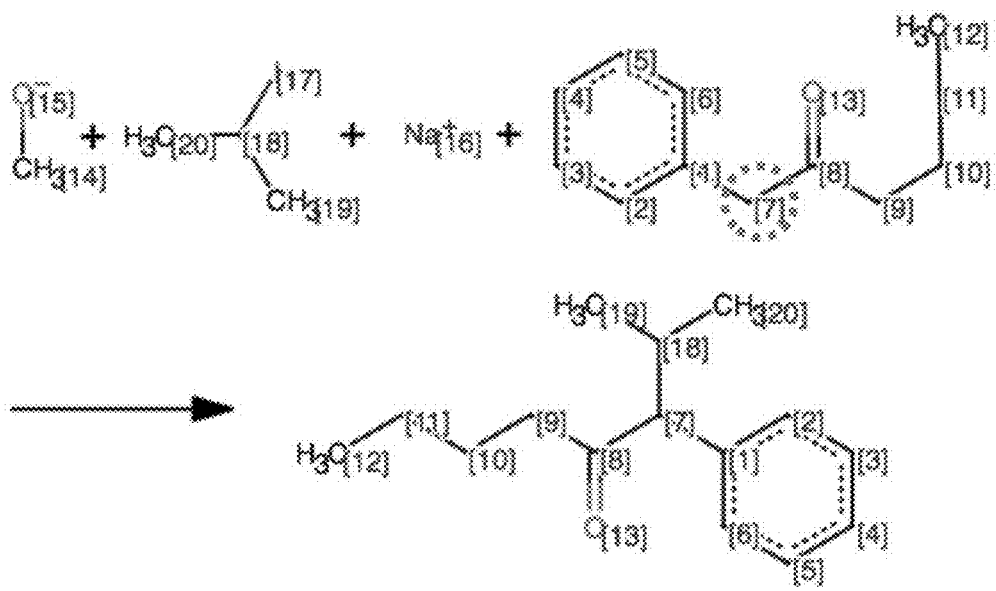
FIG. 9A is an example where reaction occurs at the a carbon (atom 7, dotted circle) of a carbonyl group (bond 8-13), also adjacent to a phenyl group (atoms 1-6). The corresponding template explicitly requires both the carbonyl and part of the phenyl ring as context (atoms 4, 7, 8, 13), although reactivity in this case does not require the additional specification of the phenyl group (atom 1).

This weakness of the baseline model can be explained by the difficulty in defining general heuristics with which to extract templates from reaction examples. It is possible to define different levels of specificity based on the extent to which atoms surrounding the reaction center are included or generalized. This introduces an unavoidable trade-off between generality (fewer templates, higher coverage, more candidates) and specificity (more templates, less coverage, fewer candidates). FIG. 9A illustrates one reaction example where the corresponding template is rare due to the adjacency of the reaction center to both a carbonyl group and a phenyl ring. Because adjacency to either group can influence reactivity, both are included as part of the template, although reactivity in this case does not require the additional specification of the phenyl group.

The massive number of templates required for high coverage is a serious impediment for the baseline approach because each template application requires solving a subgraph isomorphism problem. Specifically, it takes on average 7 seconds to apply the 5006 templates to a test instance, while our method takes less than 50 ms, about 140 times faster.

Candidate Ranking

Table 1b reports the performance on the product prediction task. Since the baseline templates from were optimized on the test and have 100% coverage, we compare its performance against our models to which the correct product is added (WLN(*) and WLDN(*)). Our model clearly outperforms the baseline by a wide margin. Even when compared against the candidates automatically computed from the reaction center, WLDN outperforms the baseline in top-1 accuracy. The results also demonstrate that the WLDN model consistently outperforms the WLN model. This is consistent with our intuition that modeling higher order dependencies between the difference vectors is advantageous over simply summing over them. Table 1b also shows that the model performance scales nicely when tested on the full USPTO dataset. Moreover, the relative performance difference between WLN and WLDN is preserved on this dataset.

Figure 9B:
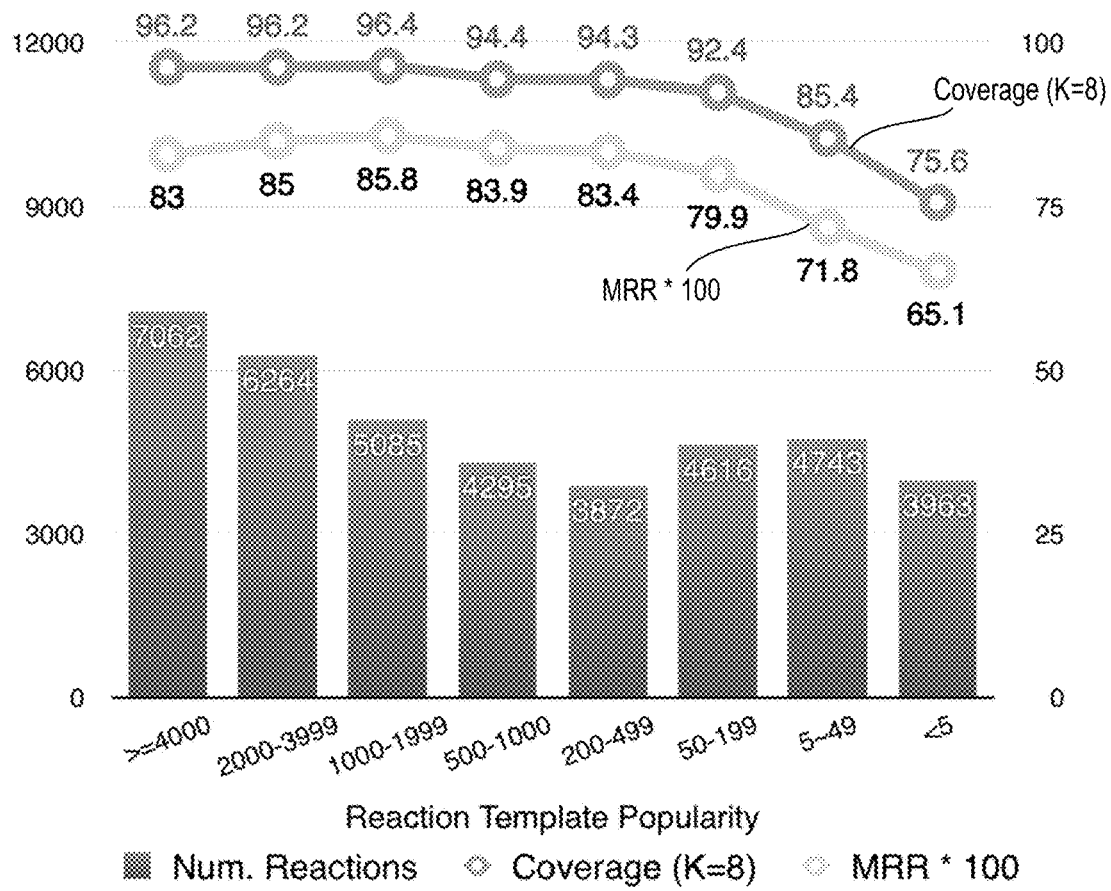
FIG. 9B are plots illustrating performance of reactions with different popularity. MRR stands for mean reciprocal rank.

We further analyze model performance based on the frequency of the underlying transformation as reflected by the number of template precedents. In FIG. 9B we group the test instances according to their frequency and report the coverage of the global model and the mean reciprocal rank (MRR) of the WLDN(*) model on each of them. As expected, the model achieves the highest performance for frequent reactions. However, it maintains reasonable accuracy even for rare reactions, which are particularly challenging for template-based methods.

Comparison with Human Performance

We randomly selected 80 reaction examples from the test set, ten from each of the template popularity intervals of FIG. 9B, and asked ten chemists to predict the outcome of each given its reactants. The average accuracy across the ten performers was 48.2%. Our model achieves an accuracy of 69.1%, outperforming even the best individual performer who scored 66.3%.

A Human Evaluation Setup

Figure 10A:
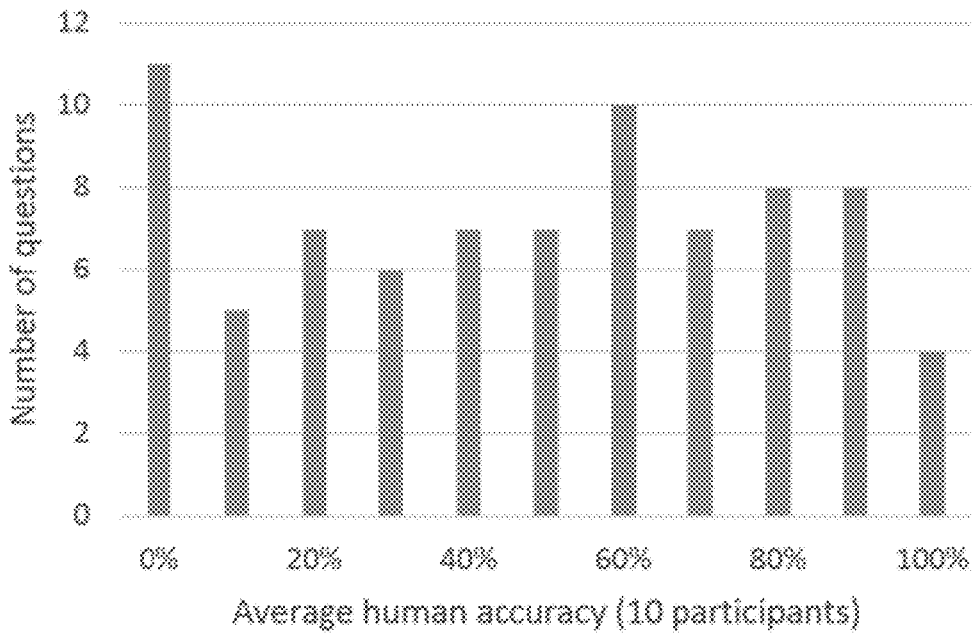
FIG. 10A is a histogram plot showing the distribution of question difficulties as evaluated by the average expert performance across all ten performers.
Figure 10B:
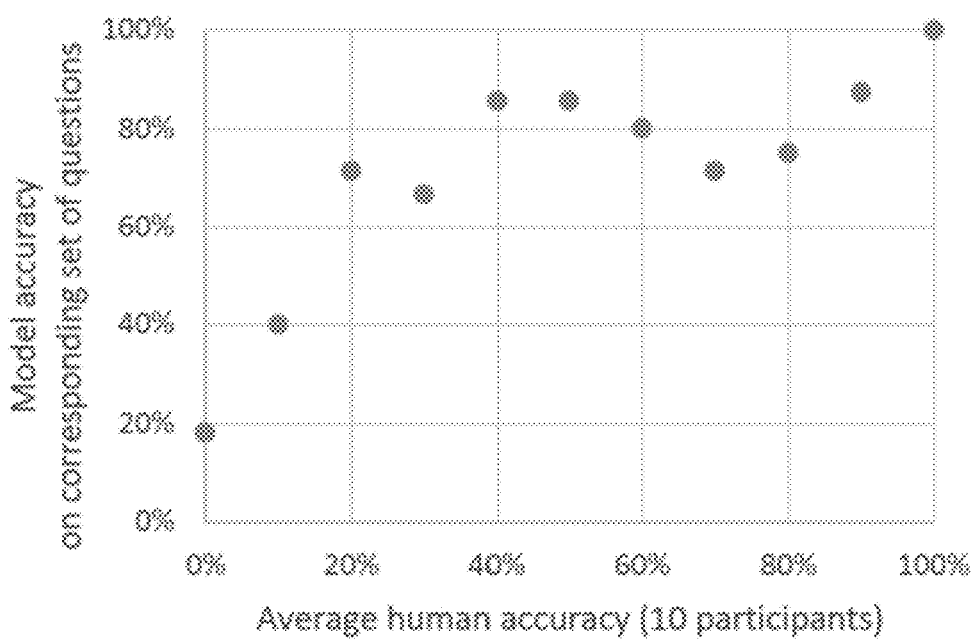
FIG. 10B is a plot comparing model performance against human performance for sets of questions as grouped by the average human accuracy shown in FIG. 10A.
Figure 10C:
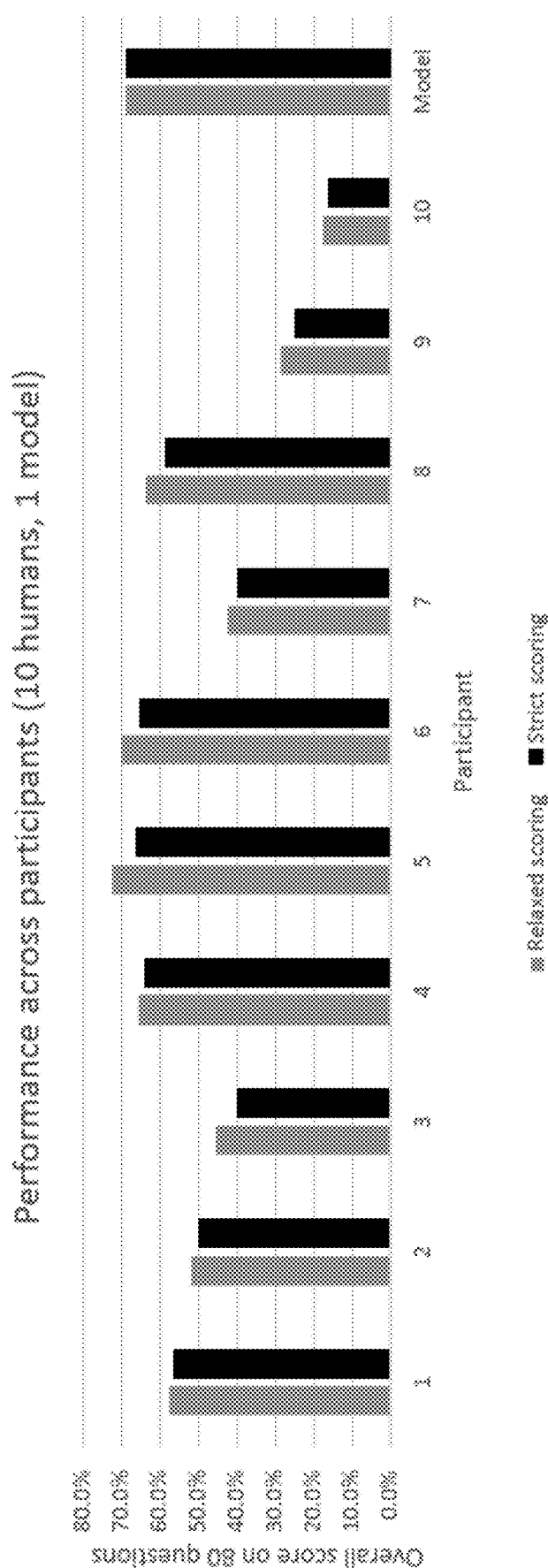
FIG. 10C is a plot of individual accuracies of each of the 10 human performers and the WLDN model. Human answers were scored for exact matches (strict scoring, also reported in Table 2) and imprecise matches (relaxed scoring), where the difference between the predicted product and the recorded product was small enough to warrant a half-point. The WLDN model performs at the expert level.

Here we describe in detail the human evaluation results in Table 2. The evaluation dataset consists of eight groups, defined by the reaction template popularity as binned in FIG. 9B, each with ten instances selected randomly from the USPTO test set. We invited in total ten chemists to predict the product given reactants in all groups. Additional details of human performance are shown in FIGS. 10A, 10B, and 10C.

a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at

TABLE 2

Human and model performance on 80 reactions randomly selected from the USPTO test set to cover a diverse range of reaction types. The first 8 are experts with rich experience in organic chemistry (graduate and postdoctoral chemists) and the last two are graduate students in chemical engineering who use organic chemistry concepts regularly but have less formal training. Our model performs at the expert chemist level in terms of top 1 accuracy.

| | | | | | | | | | | |
|---|---|---|---|---|---|---|---|---|---|---|
| Chemist | 56.3 | 50.0 | 40.0 | 63.8 | 66.3 | 65.0 | 40.0 | 58.8 | 25.0 | 16.3 |
| Our Model | | | | | 69.1 | | | | | |

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system comprising:
   at least one hardware processor; and
   at least one non-transitory computer-readable storage medium storing processor-executable instructions that, when executed by the at least one hardware processor, cause the at least one hardware processor to perform:
   obtaining input molecule information identifying at least one input molecule;
   predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center; and
   outputting information indicating the at least one output molecule.

2. The system of claim 1, wherein predicting the at least one chemical reaction further comprises identifying a chemical reaction having the at least one input molecule as at least one reactant in the chemical reaction and the at least one output molecule as at least one product in the chemical reaction.

3. The system of claim 1, wherein predicting the at least one chemical reaction further comprises identifying a chemical reaction having the at least one output molecule as at least one reactant in the chemical reaction and the at least one input molecule as at least one product in the chemical reaction.

4. The system of claim 1, wherein the at least one statistical model includes a plurality of parameters representing reactivity information for different pairs of atoms in the at least one input molecule.

5. The system of claim 1, wherein predicting the at least one chemical reaction is further performed by using at least one condition under which the at least one chemical reaction occurs, wherein the at least one condition includes at least one of temperature, pH, pressure, a type of solvent, a type of catalyst, a type of reagent, a type of buffer, a reaction time, and light irradiation.

6. The system of claim 1, wherein the at least one reaction center includes a first atom and a second atom of a first input molecule of the at least one input molecule, wherein the first atom and second atom are separated by at least one atom of the first input molecule outside the at least one reaction center.

7. The system of claim 1, wherein the at least one input molecule includes a first input molecule and a second input molecule, and the at least one reaction center includes a first atom of the first input molecule and a second atom of the second input molecule.

8. At least one non-transitory computer-readable storage medium storing processor-executable instructions that, when executed by at least one hardware processor, cause the at least one hardware processor to perform:
   obtaining input molecule information identifying at least one input molecule;
   predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center; and
   outputting information indicating the at least one output molecule.

9. The at least one non-transitory computer-readable storage medium of claim 8, wherein predicting the at least one chemical reaction further comprises:
   identifying at least one chemical bond change for the at least one reaction center that complies with a set of valence electron rules;
   determining a set of candidate output molecules based on transforming the at least one input molecule in accordance with the at least one chemical bond change; and
   identifying, from the set of candidate output molecules, the at least one output molecule.

10. The at least one non-transitory computer-readable storage medium of claim 8, wherein the at least one output molecule includes a plurality of output molecule sets, and the at least one processor is further configured to perform:
    assigning a score to each output molecule set of the plurality of output molecule sets, the assigning is performed at least in part by comparing each of the output molecule sets to the at least one input molecule;
    selecting, based on the scores for the plurality of output molecule sets, at least one output molecule set of the plurality of output molecule sets as having a likelihood of being part of a chemical reaction the includes the at least one input molecule; and
    outputting an indication of the selected at least one output molecule set.

11. The at least one non-transitory computer-readable storage medium of claim 10, wherein the assigning is further performed by:
    identifying, for each output molecule set, a plurality of values representing chemical differences between each atom in the output molecule set and the corresponding atom in the at least one input molecule; and
    determining, for each output molecule set, a score based at least in part on the plurality of values identified for the output molecule set.

12. The at least one non-transitory computer-readable storage medium of claim 8, wherein the at least one statistical model further relates properties of atoms inside and outside a region of a molecule to reactivity of the molecule at the region to identify the at least one reaction center.

13. A method, comprising:
using at least one hardware processor to perform:
obtaining input molecule information identifying at least one input molecule;
predicting at least one chemical reaction that includes a transformation between the at least one input molecule and at least one output molecule by modifying at least one reaction center of the at least one input molecule, the predicting performed at least in part by using the input molecule information and at least one statistical model relating properties of atoms outside a region of a molecule to reactivity of the molecule at the region to identify the at least one reaction center; and
outputting information indicating the at least one output molecule.

14. The method of claim 13, wherein a reaction center of the at least one reaction center identifies a set of atoms in the at least one input molecule and at least one bond type between pairs of atoms in the set of atoms.

15. The method of claim 13, wherein a reaction center of the at least one reaction center identifies a set of atoms in the at least one input molecule and a type of chemical interaction between individual pairs of atoms in the set of atoms.

16. The method of claim 15, wherein the type of chemical interaction between individual pairs of atoms in the set of atoms includes at least one of a single bond, a double bond, a triple bond, an aromatic bond, absence of a bond, and electrostatic interaction.

17. A system comprising:
at least one hardware processor; and
at least one non-transitory computer-readable storage medium storing processor-executable instructions that, when executed by the at least one hardware processor, cause the at least one hardware processor to perform:
obtaining input molecule information identifying at least one input molecule, wherein the input molecule information identifies individual atoms of the at least one input molecule and types of bonds between atoms in the at least one input molecule;
identifying at least one reaction center in the at least one input molecule, the identifying performed at least in part by using the input molecule information and at least one statistical model relating properties of atoms proximate to an atom and properties of atoms distal to the atom to reactivity of the atom; and
outputting information indicating the at least one reaction center.

18. The system of claim 17, wherein obtaining input molecule information further comprises obtaining a molecular graph representation of the at least one input molecule, wherein the molecular graph representation includes a plurality of values associated with each atom in the at least one input molecule.

19. The system of claim 18, wherein a value of the plurality of values associated with an atom indicates a likelihood of the atom to react under a set of conditions.

20. The system of claim 18, wherein a value of the plurality of values associated with an atom indicates a chemical property of the atom.

21. The system of claim 18, wherein a value of the plurality of values associated with an atom indicates structural information corresponding to the atom.

22. The system of claim 18, wherein obtaining the molecular graph representation of the at least one input molecule further comprises:
receiving an initial molecular graph representation having a plurality of nodes associated with individual atoms in the at least one input molecule and a plurality of edges associated with bonds between pairs of atoms in the at least one input molecule; and
determining, based on the initial molecular graph representation, a plurality of node labels corresponding to the plurality of nodes, wherein a node label of the plurality of node labels corresponding to an atom in the at least one input molecule includes the plurality of values associated with the atom.

23. The system of claim 22, wherein determining the plurality of node labels is performed at least in part by modifying, for a node of the plurality of nodes, the node label associated with the node based on information stored in at least one node label associated with at least one node of the plurality of nodes that neighbors the node.

24. At least one non-transitory computer-readable storage medium storing processor-executable instructions that, when executed by at least one hardware processor, cause the at least one hardware processor to perform:
obtaining input molecule information identifying at least one input molecule, wherein the input molecule information identifies individual atoms of the at least one input molecule and types of bonds between atoms in the at least one input molecule;
identifying at least one reaction center in the at least one input molecule, the identifying performed at least in part by using the input molecule information and at least one statistical model relating properties of atoms proximate to an atom and properties of atoms distal to the atom to reactivity of the atom; and
outputting information indicating the at least one reaction center.

25. The at least one non-transitory computer-readable storage medium of claim 24, wherein the at least one statistical model includes a plurality of parameters representing reactivity information for different pairs of atoms in the at least one input molecule.

26. The at least one non-transitory computer-readable storage medium of claim 24, wherein the at least one statistical model includes a plurality of parameters representing reactivity information for different pairs of atoms in the at least one input molecule that are separated by at least one atom in the same molecule.

27. The at least one non-transitory computer-readable storage medium of claim 24, wherein the at least one statistical model includes a plurality of parameters representing reactivity information for different pairs of atoms that are on two different molecules of the at least one input molecule.

28. The at least one non-transitory computer-readable storage medium of claim 24, wherein the at least one statistical model includes a plurality of parameters representing reactivity information for pairs of neighboring atoms in the at least one input molecule.

29. A method, comprising:
using at least one hardware processor to perform:
obtaining input molecule information identifying at least one input molecule, wherein the input molecule information identifies individual atoms of the at least one input molecule and types of bonds between atoms in the at least one input molecule;

identifying at least one reaction center in the at least one input molecule, the identifying performed at least in part by using the input molecule information and at least one statistical model relating properties of atoms proximate to an atom and properties of atoms distal to the atom to reactivity of the atom; and outputting information indicating the at least one reaction center.

30. The method of claim 29, wherein identifying at least one reaction center further comprises:

estimating, using the input molecule information and the at least one statistical model, reactivity information for atoms in the at least one input molecule, wherein the reactivity information includes a plurality of reactivity values associated with sets of at least two atoms in the at least one input molecule; and identifying, using the plurality of reactivity values, the at least one reaction center.

31. The method of claim 30, wherein identifying the at least one reaction center further comprises:

identifying a subset of the sets of at least two atoms in the at least one input molecule as having a reactivity value above a threshold value; and identifying the subset of the sets of at least two atoms in the at least one input molecule as the at least one reaction center.

32. The method of claim 30, wherein identifying the at least one reaction center further comprises:

ranking, based on the plurality of reactivity values, the sets of at least two atoms in the at least one input molecule;

identifying, based on the ranking, a subset of the sets of at least two atoms; and identifying the subset of the sets of at least two atoms in the at least one input molecule as the at least one reaction center.

* * * * *

UNITED STATES PATENT AND TRADEMARK OFFICE
CERTIFICATE OF CORRECTION

PATENT NO. : 10,622,098 B2
APPLICATION NO. : 16/116805
DATED : April 14, 2020
INVENTOR(S) : Connor Wilson Coley et al.

It is certified that error appears in the above-identified patent and that said Letters Patent is hereby corrected as shown below:

In the Claims

In Claim 10, at Column 30, Line 54, "chemical reaction the includes" should read --chemical reaction that includes--.

Signed and Sealed this
Twentieth Day of October, 2020

Andrei Iancu
*Director of the United States Patent and Trademark Office*